United States Patent
Reid et al.

(10) Patent No.: US 11,534,232 B2
(45) Date of Patent: Dec. 27, 2022

(54) ELECTROSURGICAL INSTRUMENT WITH OTOMY FEATURE FOR A TELEOPERATED MEDICAL SYSTEM

(71) Applicant: Intuitive Surgical Operations, Inc., Sunnyvale, CA (US)

(72) Inventors: Robert C. Reid, Fairfield, CT (US);
Adam Ross, Prospect, CT (US);
Michael Orton, Sunnyvale, CA (US);
Scott E. Manzo, Shelton, CT (US);
Benjamin J. Schoettgen, Sunnyvale, CA (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 514 days.

(21) Appl. No.: 16/492,608

(22) PCT Filed: Mar. 8, 2018

(86) PCT No.: PCT/US2018/021447
§ 371 (c)(1),
(2) Date: Sep. 9, 2019

(87) PCT Pub. No.: WO2018/165363
PCT Pub. Date: Sep. 13, 2018

(65) Prior Publication Data
US 2021/0137581 A1  May 13, 2021

Related U.S. Application Data

(60) Provisional application No. 62/470,139, filed on Mar. 10, 2017.

(51) Int. Cl.
*A61B 18/14* (2006.01)
*A61B 34/35* (2016.01)
(Continued)

(52) U.S. Cl.
CPC .......... *A61B 18/1445* (2013.01); *A61B 34/35* (2016.02); *A61B 2017/00477* (2013.01);
(Continued)

(58) Field of Classification Search
CPC ...... A61B 18/1445; A61B 2018/00595; A61B 2018/00601; A61B 2018/1455; A61B 34/35; A61B 2017/00477
See application file for complete search history.

(56) References Cited

U.S. PATENT DOCUMENTS

| 5,224,931 A | 7/1993 | Kumar |
| 8,734,445 B2 * | 5/2014 | Johnson ............ A61B 18/1445 606/51 |

(Continued)

OTHER PUBLICATIONS

International Search Report and Written Opinion for Application No. PCT/US2018/021447, dated Jun. 15, 2018, 17 pages.

(Continued)

*Primary Examiner* — Michael F Peffley
*Assistant Examiner* — Bo Ouyang
(74) *Attorney, Agent, or Firm* — Alford Law Group, Inc.; Vy H. Vu

(57) ABSTRACT

An electrosurgical end effector for a surgical tool to perform teleoperated surgical operations. The electrosurgical end effector comprises a first end effector jaw; a second end effector jaw coupled to the first end effector jaw; and a coupling pin configured to rotatingly couple the first end effector jaw to the second end effector jaw so as to cooperatively rotate open and close about an axis of rotation. The electrosurgical end effector further comprises an actuation mechanism coupled to an end of the first end effector jaw to rotate the first end effector jaw about the coupling pin; an otomy feature coupled to the second end effector jaw; and a first electrical conductor to electrically couple the otomy feature to a generator. In one embodiment, the otomy feature is electrically activated by contact with a cam portion of the first end effector jaw, when opened beyond a predetermined jaw angle.

15 Claims, 15 Drawing Sheets

(51) Int. Cl.
  *A61B 17/00* (2006.01)
  *A61B 18/00* (2006.01)
(52) U.S. Cl.
  CPC ............. *A61B 2018/0063* (2013.01); *A61B 2018/00595* (2013.01); *A61B 2018/00601* (2013.01); *A61B 2018/1455* (2013.01)

(56) References Cited

U.S. PATENT DOCUMENTS

| | | | |
|---|---|---|---|
| 2005/0137590 A1* | 6/2005 | Lawes | A61B 18/1445 606/45 |
| 2011/0034918 A1 | 2/2011 | Reschke | |
| 2012/0298719 A1* | 11/2012 | Shelton, IV | A61B 17/068 227/176.1 |
| 2013/0158542 A1 | 6/2013 | Manzo et al. | |
| 2015/0080891 A1 | 3/2015 | Shelton, IV et al. | |

OTHER PUBLICATIONS

Jelinek F., et al., "Minimally Invasive Surgical Instruments With an Accessory Channel Capable of Integrating Fibre-optic Cable for Optical Biopsy: A Review of the State of the Art," Journal of Engineering in Medicine, Aug. 2014, vol. 228 (8), pp. 843-853.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

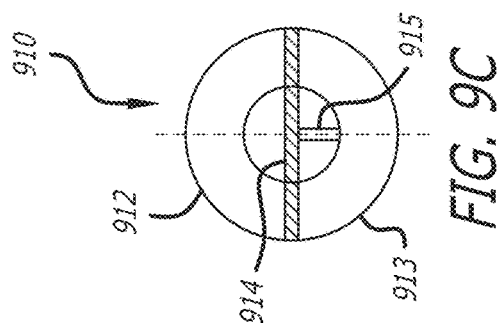
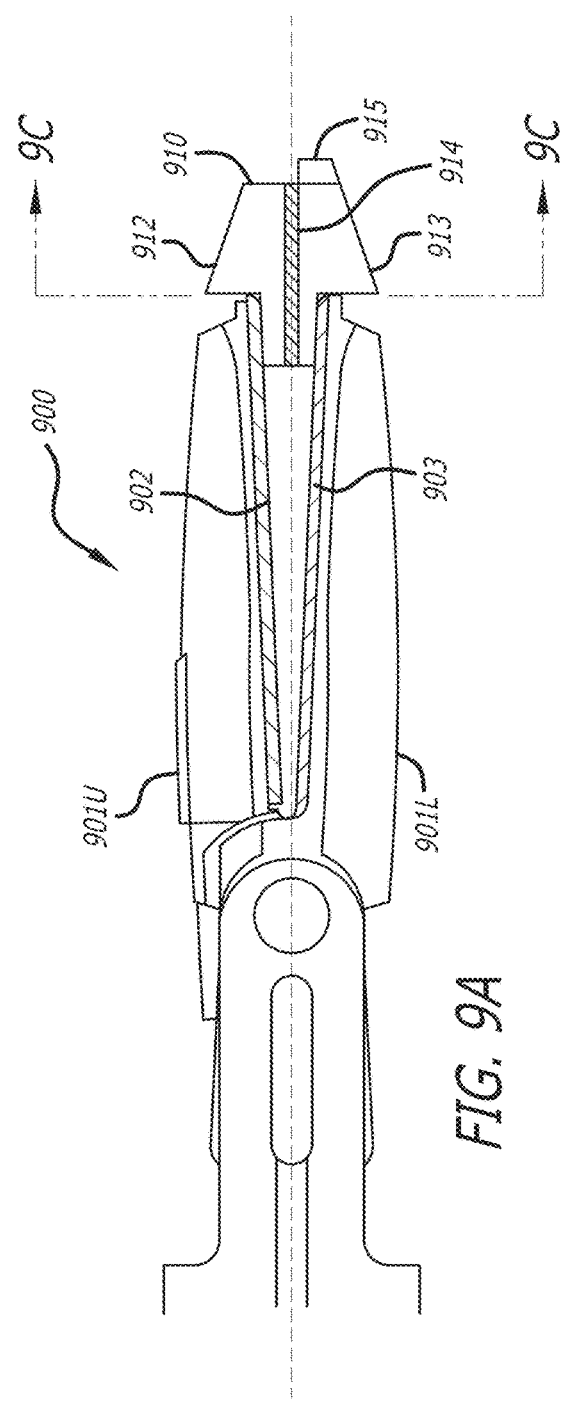
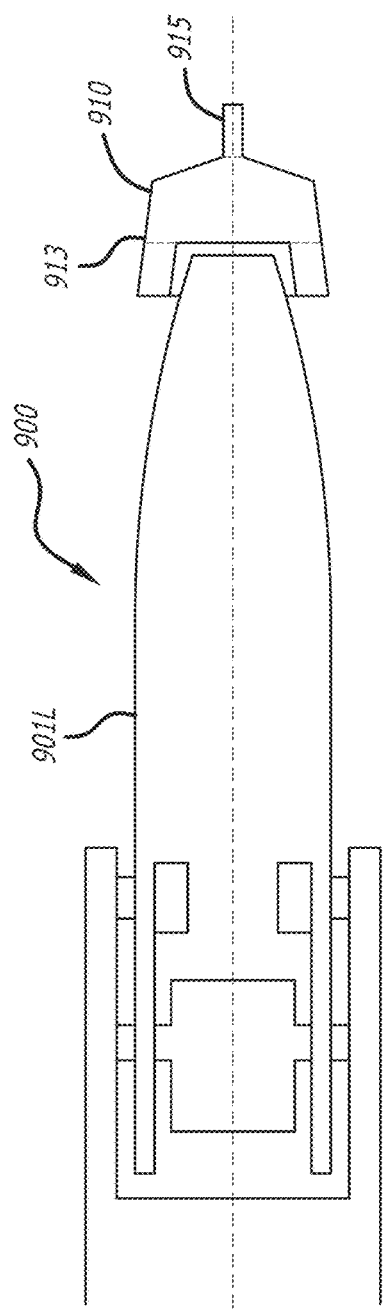

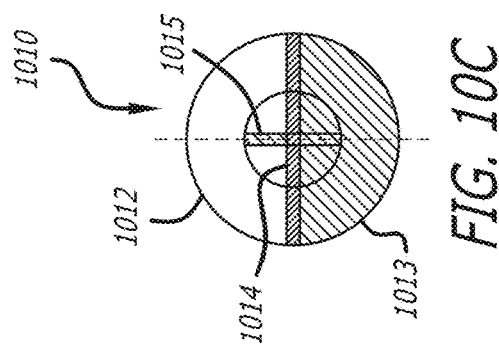
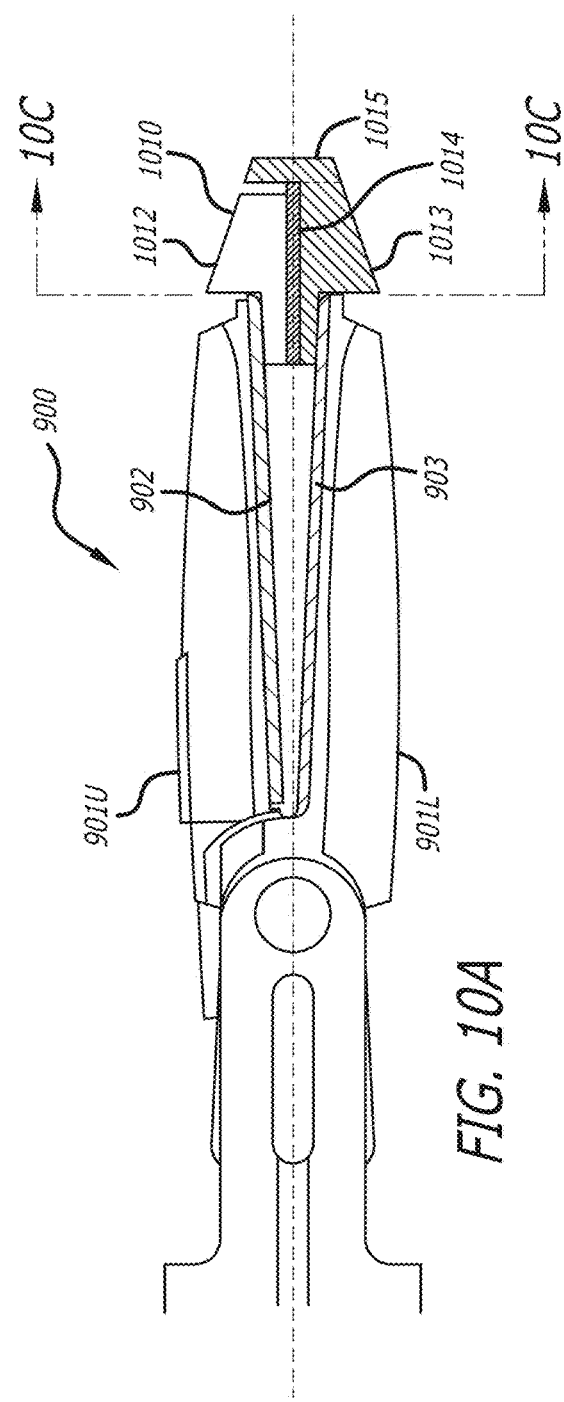
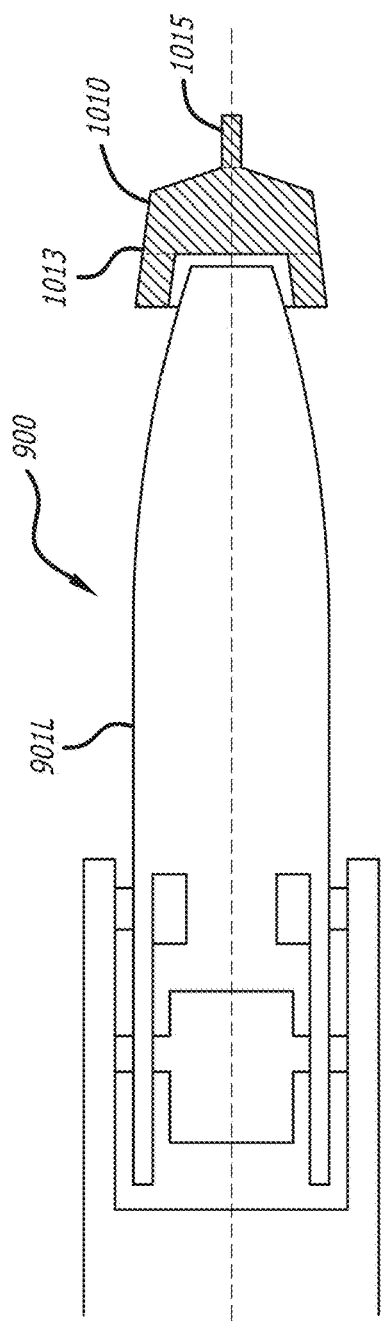
FIG. 10C
FIG. 10A
FIG. 10B

ELECTROSURGICAL INSTRUMENT WITH OTOMY FEATURE FOR A TELEOPERATED MEDICAL SYSTEM

CROSS REFERENCE TO RELATED APPLICATIONS

This U.S. Non-provisional Patent Application claims the benefit of Patent Cooperation Treaty (PCT) patent application no. PCT/US 2018/021447, entitled "ELECTROSURGICAL INSTRUMENT WITH OTOMY FEATURE FOR A TELEOPERATED MEDICAL SYSTEM", filed Mar. 8, 2018 by inventors Robert Reid et al, which in turn claims the benefit of U.S. Provisional Patent Application No. 62/470,139, similarly titled, filed on Mar. 10, 2017.

FIELD

The embodiments relate to electrosurgical tools for use in a teleoperated surgical system for minimally invasive surgical operations.

BACKGROUND

Minimally invasive surgical techniques generally reduce the amount of extraneous tissue damage during surgical procedures, thereby reducing patient recovery time, discomfort, and deleterious side effects. One effect of minimally invasive surgery, for example, is reduced post—operative hospital recovery times. Because the average hospital stay for a standard surgery is typically significantly longer than the average stay for an analogous minimally invasive surgery, increased use of minimally invasive techniques could save millions of dollars in hospital costs each year. Patient recovery times, patient discomfort, surgical side effects, and time away from work can also be reduced by increasing the use of minimally invasive surgery.

Traditional forms of minimally invasive surgery typically include endoscopy, which is visual examination of a hollow space with a viewing instrument called an endoscope. One of the more common forms of endoscopy is laparoscopy, which is a visual examination and/or treatment in the abdominal cavity. In traditional laparoscopic surgery a patient's abdominal cavity is insufflated with gas and cannula sleeves are passed through small incisions in the musculature of the patient's abdomen to provide entry ports through which laparoscopic surgical instruments can be passed in a sealed fashion. Such incisions are typically about one half of an inch (about 12 mm) in length to minimize recovery time.

Traditional manual laparoscopic surgical instruments generally include a laparoscope with a video camera for viewing the surgical field and working tools defining end effectors. Typical surgical end effectors include clamps, graspers, scissors, staplers, and needle holders, for example. The type of working tools are similar to those used in conventional (open) surgery, except that the working end or end effector of each tool is separated from its manual handle by a long extension tube, typically of about 12 inches (about 300 mm) in length, for example, so as to permit the surgeon to introduce the end effector to the surgical site and to control movement of the end effector relative to the surgical site from outside a patient's body.

To perform a surgical procedure, a surgeon typically passes the working tools or instruments through the cannula sleeves to the internal surgical site and manipulates the instruments from outside the abdomen by sliding them in and out through the cannula sleeves, rotating them in the cannula sleeves, levering (i.e., pivoting) the instruments against the abdominal wall, and actuating the end effectors on distal ends of the instruments from outside the abdominal cavity. The instruments normally pivot around centers defined by the incisions which extend through the muscles of the abdominal wall. The surgeon typically monitors the procedure by means of a television monitor which displays an image of the surgical site captured by the laparoscopic camera. Typically, the laparoscopic camera is also introduced through the abdominal wall so as to capture the image of the surgical site. Similar endoscopic techniques are employed in, for example, arthroscopy, retroperitoneoscopy, pelviscopy, nephroscopy, cystoscopy, cisternoscopy, sinoscopy, hysteroscopy, urethroscopy, and the like.

Although traditional minimally invasive surgical instruments and techniques like those just described have proven highly effective, newer systems may provide even further advantages. For example, traditional minimally invasive surgical instruments often deny the surgeon the flexibility of tool placement found in open surgery. Difficulty is experienced in approaching the surgical site with the instruments through the small incisions. Additionally, the added length of typical endoscopic instruments often reduces the surgeon's ability to feel forces exerted by tissues and organs on the end effector. Furthermore, coordination of the movement of the end effector of the instrument as viewed in the image on the television monitor with actual end effector movement is particularly difficult, since the movement as perceived in the image normally does not correspond intuitively with the actual end effector movement. Accordingly, lack of intuitive response to surgical instrument movement input is often experienced. Such a lack of intuitiveness, dexterity, and sensitivity of endoscopic tools has been found to be an impediment in the increased use of minimally invasive surgery.

Teleoperated surgical systems have been developed to increase surgical dexterity as well as to permit a surgeon to operate on a patient in an intuitive manner. Teleoperated surgery is a general term for surgical operations using systems where the surgeon uses some form of remote control, e.g., a servomechanism, or the like, to manipulate surgical instrument movements, rather than directly holding and moving the tools by hand. In such a teleoperated surgical system, the surgeon is typically provided with an image of the surgical site on a visual display at a location that may be remote from the patient. An imaging tool such as an endoscope with a stereo video camera can be used to view the surgical area, and the image captured by the imaging tool can be displayed on the visual display device. The surgeon can typically perform the surgical procedure at the location remote from the patient while viewing the end effector movement on the visual display during the surgical procedure. While typically viewing a three-dimensional image of the surgical site on the visual display device, the surgeon manipulates master control devices at the remote location which controls motion of the remotely controlled or teleoperated instruments.

Typically, such a teleoperated surgical system can be provided with at least two master control devices (one for each of the surgeon's hands), which are operatively associated with a plurality of teleoperated arms on which a surgical instrument is mounted. Operative communication between master control devices and associated teleoperated surgical arm and instrument assemblies is typically achieved through a control system. The control system typically includes at least one processor which relays input commands from the master control devices to the associated teleoperated arm and instrument assemblies and from the arm and instrument assemblies to the associated master control devices in the case of, e.g., force feedback, or the like.

Teleoperated surgical systems may perform a wide variety of surgical procedures using different surgical tools. For example, to perform electrosurgery, electrosurgical tools may be coupled to the teleoperated arms of the teleoperated surgical system. Electrosurgery refers broadly to a class of medical procedures which rely on the application of high frequency electrical energy to patient tissue to achieve a number of possible effects, such as cutting, coagulation, desiccation, and the like. A typical electrosurgical instrument is capable of treating tissue of an organism with the use of heat produced by electrical energy passing through tissue.

Electrosurgical tools include monopolar electrosurgical tools, bipolar electrosurgical tools, harmonic tools, laser tools, ultrasound tools. Electrosurgical tools, used in teleoperated surgery, are mechanically coupled to a teleoperated arm to control its movement; they are also coupled to an electrosurgical generator so that energy may be applied to tissue at or near its end effectors. For example, in some minimally invasive and teleoperated surgical procedures, tissue in the patient's body must be cauterized and severed. To perform such a procedure, bipolar or monopolar cauterizing grips can be introduced through a trocar to engage the target tissue. Electrical energy, such as radio frequency energy, is delivered to the grips to cauterize the engaged tissue.

Electrical energy delivery may be carried out before, during, and/or after tissue shearing. The delivered electrical energy produces heat capable of treating the tissue. For example, the heat may cauterize the tissue or coagulate blood so as to minimize bleeding during a treatment procedure. Electrosurgical tools may use high frequency alternating currents (AC) such as radio frequency (RF) energy to provide the heat necessary for cauterization and coagulation. High frequency RF energy is preferred to minimize muscular contractions and electrocution. Monopolar devices are typically used in conjunction with a grounding pad wherein one pole of an electrosurgical generator is mounted to the instrument and the other pole is mounted to the grounding pad. The electrical current from a monopolar electrosurgical generator travels into the monopolar instrument, through the patient's body to the grounding pad, and back to the generator. Bipolar instruments are typically connected to both poles of the bipolar electrosurgical generator. Current flow in a patient's body with bipolar devices is typically limited to the tissue near the working end of the bipolar instrument, thereby reducing the risk of damaging non-target tissue.

Minimally invasive teleoperated instruments generally pass through a small incision in the patient and the surgery takes place in a body cavity. As such, there is a limit to the number of surgical instruments that can fit inside the limited space. It is desirable, therefore, to provide teleoperational surgical tools with multiple functionalities. The systems and methods disclosed herein overcome one or more of the deficiencies of the prior art.

During surgery it may be desired to use a surgical instrument to create holes or perforations in tissue of certain target anatomy (e.g. stomach, bowel, or mesentery). Typically this incision, referred to as an otomy, derived from gastrotomy, enterotomy, etc., is achieved using a monopolar energy instrument such as a hook, spatula or monopolar curved scissor (MCS); an advanced energy instrument incorporating a monopolar tip; or an ultrasonic shear. These conventional instruments pose a risk to the patient because their otomy creating feature is generally active or hot and can cause tissue damage if the otomy creating feature accidently contacts the patient. It is desirable, therefore, to provide safer teleoperational surgical tools with selective otomy creating functionality.

BRIEF SUMMARY OF THE INVENTION

The embodiments of the invention are summarized by the claims that follow below.

BRIEF DESCRIPTION OF THE DRAWINGS

FIGS. 9A-9D illustrate an otomy accessory tool for use with a bipolar surgical instrument.

FIGS. 10A-10D illustrate an otomy accessory tool for use with a bipolar surgical instrument.

DETAILED DESCRIPTION OF THE INVENTION

Figure 1A:
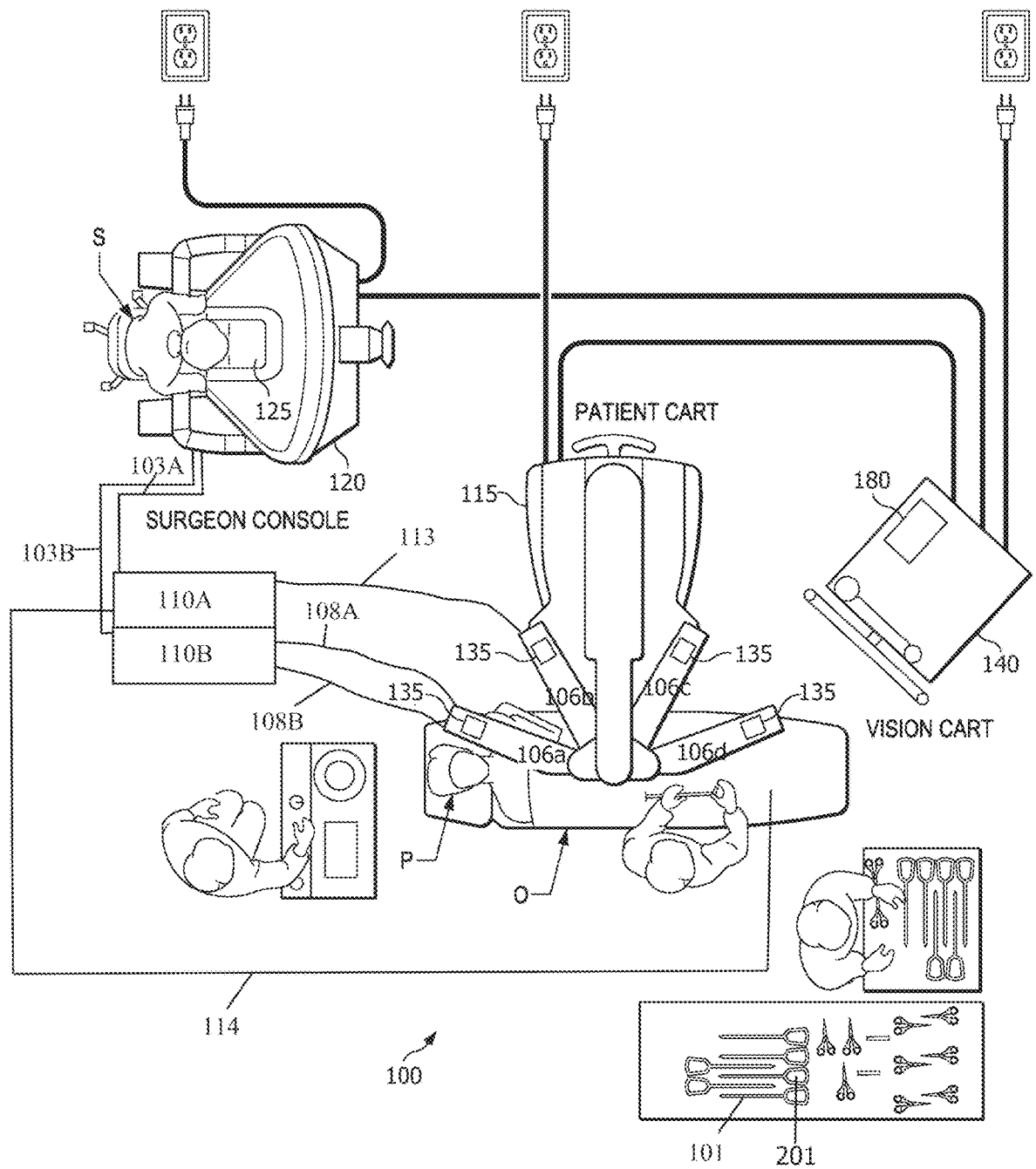
FIG. 1A illustrates an exemplary teleoperational surgical system according to one embodiment of the present disclosure.

In the following detailed description of the embodiments of the invention, numerous specific details are set forth in order to provide a thorough understanding of the embodiments of the invention. However, it will be obvious to one skilled in the art that the embodiments of the invention may be practiced without these specific details. In other instances well known methods, procedures, components, and circuits have not been described in detail so as not to unnecessarily obscure aspects of the embodiments of the invention. No limitation of the scope of the disclosure is intended by these detailed descriptions.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. The numerous iterations of these combinations will not be described separately. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For simplicity, in some instances the same reference numbers are used throughout the drawings to refer to the same or like parts.

Introduction

Teleoperated surgery may be used to perform a wide variety of surgical procedures, including but not limited to open surgery, neurosurgical procedures (such as stereotaxy), endoscopic procedures (such as laparoscopy, arthroscopy, thoracoscopy), and the like. During these teleoperated surgical procedures, surgeons may use high voltage, low current electrical energy of various wave forms to perform such tasks as cautery, cutting tissue, or sealing a vessel. Electrical energy supply devices (also referred to as electrosurgical generators) are coupled to surgical instruments and are typically activated by a foot pedal switch of a foot pedal. One or more foot pedals in a surgeon's console and their corresponding switches may be used to activate these electrical energy supply devices.

The invention provides methods, systems, and apparatus for use in teleoperated minimally invasive surgical operations. In particular, electrosurgical cutting/shearing instruments and systems, as well as methods of performing minimally invasive teleoperated surgical procedures with such instruments are disclosed. The disclosed instruments are capable of treating tissue with heat produced by electrical energy while cutting, sealing, perforating, shearing, grasping, engaging, or contacting treatment tissue. The electrosurgical treatment may further reduce bleeding of tissue by cauterizing tissue and coagulating blood, or achieve various other desired effects on the treatment tissue. By providing electrosurgical cutting/shearing instruments for use with a teleoperated surgical system, apparatus and methods enable the advantages associated with electrosurgical cutting/shearing treatment to be combined with the advantages of a minimally invasive teleoperated surgery.

The disclosed embodiments relate to an electrosurgical tool for use with a minimally invasive teleoperated surgical system. The electrosurgical tool comprises an elongated hollow shaft having a proximal end and a distal end. An end effector for performing the surgical procedure, e.g. cutting, shearing, perforating, cauterizing, grasping, etc., is coupled to the distal end of the shaft. An interface or tool base is coupled to the proximal end of the shaft.

The interface base generally includes one or more mechanical transmission members configured to engage one or more drivers of the teleoperated surgical system. For example, in a jawed end effector, the transmission members transmit forces from the teleoperated surgical system to the end effector via one or more actuation elements so as to pivotally move the jaws. The elongate shaft defines an internal longitudinally extending passage, the actuation element being slideably housed within the passage extending internally along the shaft. The actuation or articulation element may comprise an actuator rod coupled to a connector rod which in turn couples each jaw. Alternatively a system of pulleys may actuate the connector rod to open and close the jaws. Actuation of the actuator rod and connector rod in a distal direction relative to the shaft moves the jaws apart from one another and actuation of the actuator rod and connector rod in a proximal direction relative to the shaft moves the jaws together.

Opposite the interface base, coupled to a distal end of the shaft, is an end effector. An end effector is designed to perform a surgical operation such as cutting, shearing, perforating, grasping, engaging, contacting tissue to cauterize and desiccate, etc. In embodiments of the invention, the end effector generally comprises a pair of jaws rotating open and close about an axis of rotation similar to the mechanical action of a pair of shears. The jaws further comprise one or more electrodes electrically communicating with a conductor to deliver electrical energy to tissue. The electrode may be used to create holes in target anatomy e.g. stomach, bowel, or mesentery. As such, the electrode may be referred to as an "otomy creating feature", "otomy feature", or an "otomy tip".

The disclosed embodiments may feature an otomy tip that is present but not active. During normal use of the end effector, the otomy tip is physically present but is electrically floating such that electrical energy does not conduct to the patient. When the otomy tip is needed to perform a perforation or other surgical procedure, an electrical connection is made between the otomy tip an a generator and electrical energy is delivered to tissue via the otomy tip.

Other embodiments may feature an otomy tip that is not always present but is electrically active even during normal use of the surgical end effector. During normal use, the otomy tip may be shrouded in a nonconductive cover or layer and kept from physical and electrical contact with the patient. However, while shrouded, the otomy tip would be electrically active. If a perforation or other surgical procedure requiring an otomy tip is needed, the otomy tip may be mechanically actuated to protrude from the shroud.

In yet other embodiments, the otomy tip may not be extended or activated during normal use of the surgical end effector. During normal use, the otomy tip may be shrouded or hidden to keep it from physically contacting the patient. Additionally the otomy tip may be kept electrically inactive even while physically shrouded. When an otomy procedure is desired, the otomy tip physically protrudes from the shroud and then is electrically activated.

Other embodiments of the invention involve methods for performing minimally invasive teleoperated surgical procedures with the electrosurgical instruments described above. One method includes connecting a surgical instrument to a teleoperated surgical system. Connecting the surgical instrument to a teleoperated surgical system further includes releasably mounting the surgical instrument on a teleoperated surgical arm. Passing the surgical instrument, having an elongate shaft at one end of which an end effector is mounted, through an entry port in a patient body, and contacting tissue with the end effector. Delivering electrical energy to an otomy feature on the end effector and perforating a hole in the contacted tissue.

Teleoperated Surgical Systems

Teleoperated surgery generally involves the use of a robot manipulator that has multiple teleoperated manipulator arms. One or more of the teleoperated manipulator arms often support a teleoperated surgical tool or instrument which may be an electrosurgical tool or a non-electrosurgical tool. One or more of the teleoperated manipulator arms are often used to support a surgical image capture device such as an endoscope (which may be any of a variety of instruments such as a laparoscope, an arthroscope, a hysteroscope, or the like), or, optionally, some other imaging modality (such as ultrasound, fluoroscopy, magnetic resonance imaging, or the like). Typically, the teleoperated manipulator arms will support at least two teleoperated surgical tools (corresponding to the two hands of a surgeon) and one image capture device.

Referring now to FIG. 1A, a teleoperational medical system 100 for use in, for example, medical procedures including diagnostic, therapeutic, or surgical procedures, is shown. As will be described, the teleoperational medical systems of this disclosure are under the teleoperational control of a surgeon. In alternative embodiments, a teleoperational medical system may be under the partial control of a computer that is programmed to perform a procedure or a sub-procedure. In still other alternative embodiments, a fully automated medical system may be under the full control of a computer may be programmed to perform procedures or sub-procedures.

As shown in FIG. 1A, the teleoperational medical system 100 generally includes a teleoperational assembly 115 near or mounted to an operating table O on which a patient P is positioned. The teleoperational assembly 115 may be referred to as a patient-side manipulator (PSM) or patient side cart. The teleoperational assembly 115 is operably coupled to and forms a part of teleoperational medical system 100. An operator input system 120 allows a surgeon or other type of clinician S to view images of or representing the surgical site and to control the operation of the teleoperational assembly 115. The operator input system 120 may be referred to as a master or surgeon's console. One example of a teleoperational surgical system that can be used to implement the systems and techniques described in this disclosure is a da Vinci® Surgical System manufactured by Intuitive Surgical, Inc. of Sunnyvale, Calif.

The teleoperational assembly 115 and its surgical instrument 101 may include a kinematic structure of one or more non-servo controlled links (e.g., one or more links that may be manually positioned and locked in place, generally referred to as a set-up structure) and a teleoperational manipulator. (See, e.g., FIG. 2) The teleoperational assembly 115 includes a plurality of motors that drive inputs on the surgical instrument 101. These motors move in response to commands from a vision cart 140. The motors include drive systems which when coupled to the surgical instrument 101 may advance the surgical instrument 101 into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument. The teleoperational assembly 115 may be configured and arranged to sense, detect, calculate, or otherwise determine the position of each motor and/or each arm. The teleoperational assembly 115 may include a user interface configured to receive information from and convey information to a user.

In some embodiments, the user interface is a touchpad interface that may present information to the user during guided setup of the teleoperational medical system 100. The teleoperational assembly 115 includes elements 135, such as sensors, switches, encoders, and/or other components that sense the arrangement of components of the teleoperational assembly. The arrangement may include the presence or absence of components as provided in the examples below or may include the physical relative position of components. The vision cart 140 is operatively linked to the touchpad, sensors, motors, actuators, encoders, hydraulic flow systems, and other components of the teleoperational assembly 115, the operator input system 120 and to an image capture system. The image capture system includes an image capture device, such as an endoscope that may be carried on the surgical instrument 101 of the teleoperational assembly 115, and related image processing hardware and software.

The operator input system 120 may be located at a surgeon's console, which may be located in the same room as operating table O. It should be understood, however, that the surgeon S can be located in a different room or a completely different building from the patient P. Operator input system 120 generally includes one or more control device(s) for controlling the surgical instrument 101. More specifically, in response to the surgeon's input commands, the vision cart 140 effects servo mechanical movement of the surgical instrument 101. The control device(s) may include one or more of any number of a variety of input devices, such as hand grips, joysticks, trackballs, data gloves, trigger-guns, hand operated controllers, foot-operated controllers, voice recognition devices, touchscreens, body motion or presence sensors, and the like.

In some embodiments, the control device(s) will be provided with the same degrees of freedom as the medical instruments of the teleoperational assembly to provide the surgeon with telepresence, the perception that the control device(s) are integral with the instruments so that the surgeon has a strong sense of directly controlling instruments as if present at the surgical site. In other embodiments, the control device(s) may have more or fewer degrees of freedom than the associated medical instruments and still provide the surgeon with telepresence. In some embodiments, the control device(s) are manual input devices which move with six degrees of freedom, and which may also include an actuatable handle for actuating instruments (for example, for closing grasping jaws, applying an electrical potential to an electrode, delivering a medicinal treatment, and the like).

The vision cart 140 includes at least one memory and at least one processor 180, and typically a plurality of processors, for effecting control between the teleoperational assembly 115, surgical instrument 101, the operator input system 120, the image capture system, and the display system 125. The vision cart 140 also includes programmed instructions (e.g., a computer-readable medium storing the instructions) to implement some or all of the methods described in accordance with aspects disclosed herein. While vision cart 140 is shown as a single contained element in FIG. 1, the system may include two or more data processing circuits with one portion of the processing optionally being performed on or adjacent the teleoperational assembly 115, another portion of the processing being performed at the operator input system 120, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, vision cart 140 supports wireless communication protocols such as Bluetooth, IrDA, HomeRF, IEEE 802.11, DECT, and Wireless Telemetry.

The system operator sees images, captured by the image capture system, presented for viewing on a display system 125 operatively coupled to or incorporated into the operator input system 120. The display system 125 displays an image or representation of the surgical site and medical instrument system(s) as generated by sub-systems of the image capture system. The display system 125 and the operator input system 120 may be oriented so the operator can control the operator input system 120 with the perception of telepresence. The display system 125 may include multiple displays such as separate right and left displays for presenting separate images to each eye of the operator, thus allowing the operator to view stereo images.

Alternatively or additionally, display system 125 may present images of the surgical site recorded and/or imaged preoperatively or intra-operatively using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and the like. The presented preoperative or intra-operative images may include two-dimensional, three-dimensional, or four dimensional (including, e.g., time based or velocity based information) images and associated image data sets for reproducing the images.

The vision cart 140 also includes a user interface that is configured to receive information from and convey information to a user. In the embodiments described herein, the user interface may comprise a touchscreen monitor that may present prompts, suggestions, and status update during the guided setup process. In some embodiments, the touchscreen monitor is disposed in a position in the operating room where it can be easily seen as a user sets up the teleoperational assembly 115. This may be within a sterile zone of the system. In contrast, the touchpad on the teleoperational assembly 115 may be disposed at a location outside the sterile zone, and may be accessed by a non-sterile person during the guided setup. In another embodiment, both the touchpad and the touchscreen monitor are in the sterile zone. While described as a touchscreen monitor, other embodiments may comprise other user interfaces e.g. one or monitors or display screens, a keyboard, a computer mouse, rollers, buttons, knobs, etc.

The guided setup disclosed herein may be one or more computer programs executed on the vision cart 140 for dynamically assisting a user with setup of the teleoperational assembly 115. In some embodiments, the guided setup is executed on any of a wide variety of centralized or distributed data processing architectures. It may also be implemented as a number of separate programs or subroutines, or may be integrated into a number of other aspects of the teleoperational systems described herein.

In some embodiments, the vision cart 140 may include one or more servo controllers that receive force and/or torque feedback from the teleoperational assembly 115. Responsive to the feedback, the servo controllers transmit signals to the operator input system 120. The servo controller(s) may also transmit signals instructing teleoperational assembly 115 to move the surgical instrument 101 which extend into an internal surgical site within the patient body via openings in the body. Any suitable conventional or specialized servo controller may be used. A servo controller may be separate from, or integrated with, teleoperational assembly 115. In some embodiments, the servo controller and teleoperational assembly are provided as part of a teleoperational arm cart positioned adjacent to the patient's body.

The teleoperational medical system 100 may further include optional operation and support systems (not shown) such as illumination systems, steering control systems, eye tracking systems, fluid management systems such as irrigation systems and/or suction systems. In alternative embodiments, the teleoperational system may include more than one teleoperational assembly and/or more than one operator input system. The exact number of manipulator assemblies will depend on the surgical procedure and the space constraints within the operating room, among other factors. The operator input systems may be collocated or they may be positioned in separate locations. Multiple operator input systems allow more than one operator to control one or more manipulator assemblies in various combinations.

To support the functionality of the electrosurgical tools 201, the teleoperated surgical system 100 may further include one or more electrosurgical generators 110A-110B. The one or more electrosurgical generators 110A-110B are remotely controlled by the master console 120 over the control cable 103A,103B by a surgeon operating the master console 120.

The surgeon may activate an input, such as a foot switch, causing the generator to supply electrical energy through a power cord and the conductor to the end effector. Typically a high frequency AC or RF current may be employed, with the voltage being dependent on the type and degree of treatment desired. Voltages may range up to 12,000V in some cases, with about 3000V being a typical value, e.g., for coagulation in monopolar instruments and lower voltages of about 500V for cutting with bipolar instruments.

The conductor generally provides electrosurgical treatment in a safe and effective manner that minimizes current leakage as the conductor is largely insulated from the tool base to the distal end of the shaft. The invention incorporates a variety of safety features to prevent current leakage to non-target tissue so as to reduce collateral tissue damage, unwanted burning, or the like. Unintended current leakage can be minimized or prevented by insulating the conductor within the elongate shaft and by extending the conductor to the electrode. The area adjacent to the point of contact with the electrode may be potted to prevent current leakage.

In one embodiment, the electrosurgical generator 110B is a bipolar generator. A pair of wires 108A and 108B couple between the bipolar electrosurgical generator 110B and a bipolar electrosurgical tool 201. The pair of wires 108A-108B may transfer the energy of the bipolar electrosurgical generator 110B to a respective end effector of the bipolar electrosurgical tool 201 to cauterize, perforate, seal, desiccate or cut tissue. The electrosurgical tool 201 is mounted to one or more surgical arms 106a-d. The electrosurgical tool 201 is a subset of surgical tool 101 and has electrosurgical functionality.

In other embodiments, the electrosurgical generator 110A is a monopolar generator. A wire 113 couples between the monopolar electrosurgical generator 110A and a monopolar electrosurgical tool 201. A ground wire 114 couples between the monopolar electrosurgical generator 110A and patient P. The wire 113 may transfer the energy of the monopolar electrosurgical generator 110A to an end effector of the monopolar electrosurgical tool 201 to cauterize, perforate, seal, desiccate or cut tissue.

A monopolar electrosurgical generator and a bipolar electrosurgical generator may be combined together into one electrosurgical generator that can be remotely controlled by two sets of controls from the control console 120. That is, a first set of controls can be used to control one function of the remote controlled equipment to supply (e.g., monopolar electrosurgical energy) to a first teleoperated surgical tool while a second set of controls of the equipment can be used to control another function of the remote controlled equipment to supply (e.g., bipolar electrosurgical energy) to a second surgical tool.

The remote controlled equipment may also be referred to as remote controllable equipment or remote controlled supply equipment. The surgical tools that couple to the remote controlled equipment to receive a supply may also be referred to as supply controllable tools.

Figure 1B:
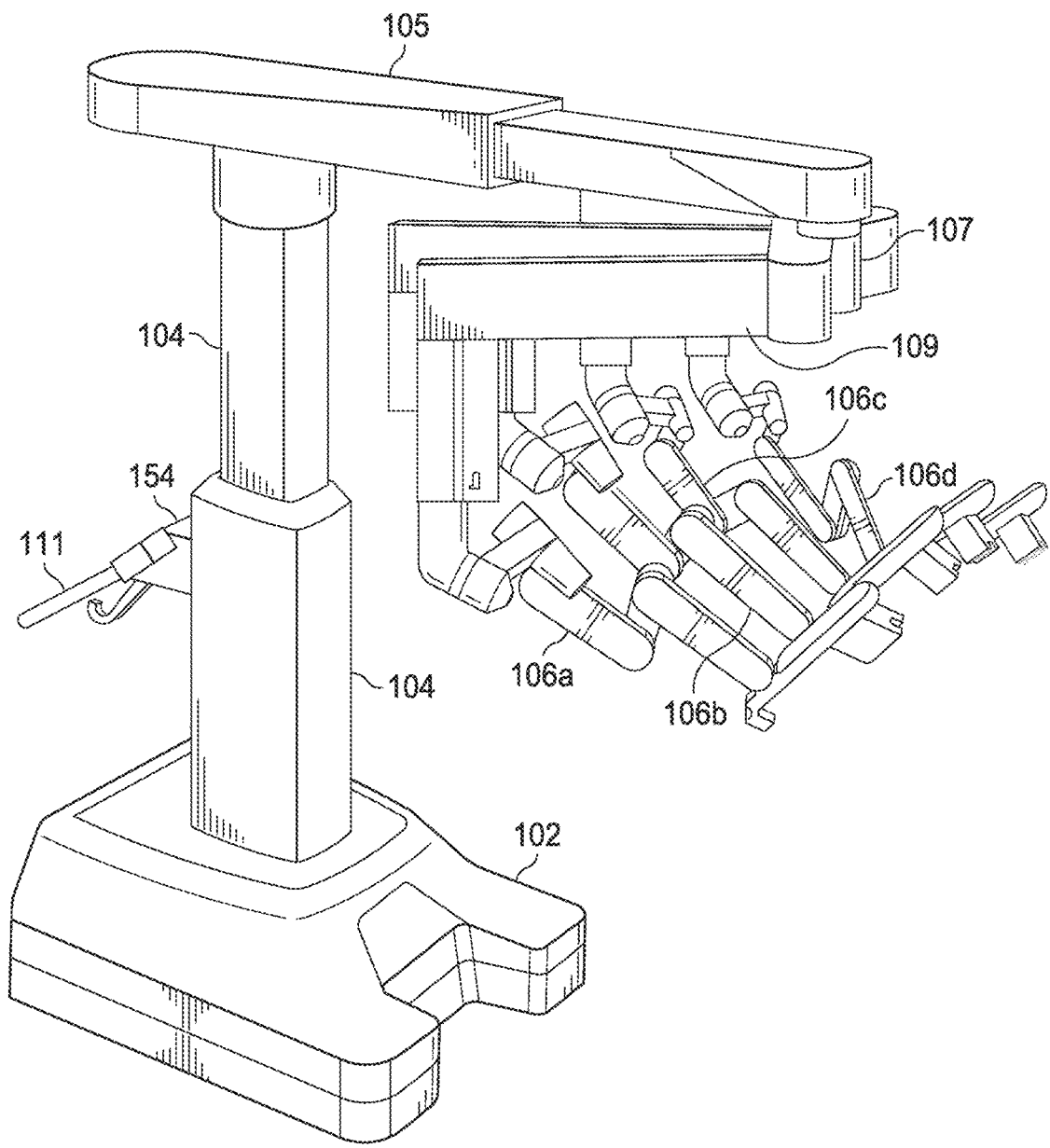
FIG. 1B illustrates a front perspective view of an exemplary teleoperational assembly according to one embodiment of the present disclosure.

FIG. 1B shows an exemplary teleoperational assembly 115 (e.g., the teleoperational assembly 115 shown in FIG. 1A) according to one embodiment. The assembly 115 includes an automated and motorized setup structure that supports projecting arms, and may include a base 102 that rests on the floor, a telescoping support column 104 that is mounted on the base 102, a telescoping boom 105 that extends from the support column 104, and a platform portion as an orienting platform 107. The assembly 115 also includes support beams 109, and several arms 106a-d that support surgical tools (including portions of the image capture system e.g. an endoscope). As shown in FIG. 1B, arms 106a, 106b, 106c, 106d are instrument arms that support and move the surgical instruments used to manipulate tissue. One of these arms 106a-d may be designated as a camera arm that supports and moves an endoscope. In other embodiments the endoscope may be combined with other surgical tools to save space.

Figure 1C:
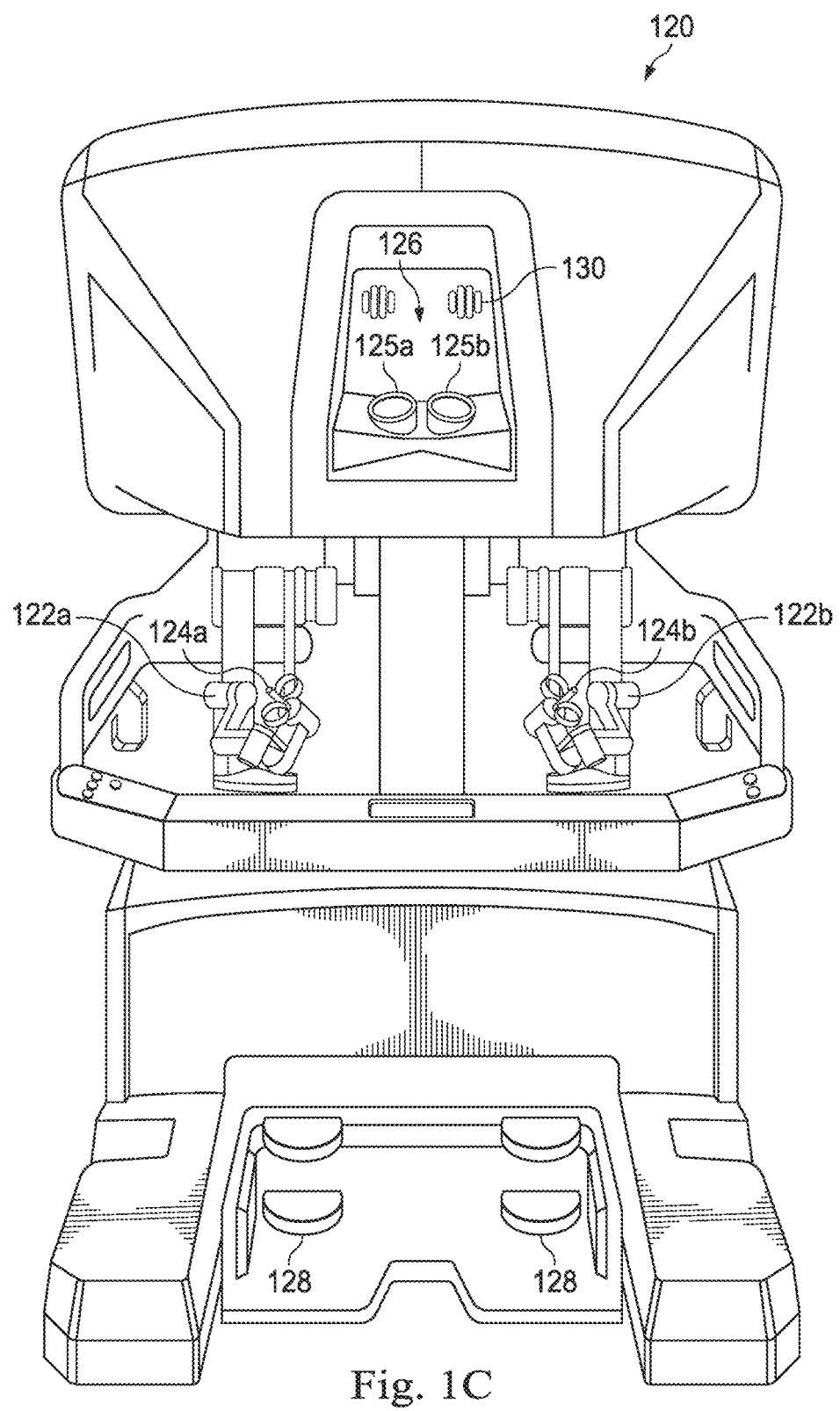
FIG. 1C illustrates a front perspective view of an exemplary operator input console according to one embodiment of the present disclosure.

FIG. 1C is a slightly elevated frontal view of an operator input system 120 (e.g., the operator input system 120 shown in FIG. 1A). The operator input system 120 includes a console 120 equipped with left and right multiple degree-of-freedom (DOF) control interfaces 122a and 122b, which are kinematic chains that are used to control the surgical instruments 101 (See FIG. 1E) including the endoscope. The surgeon grasps a pincher assembly 124a, 124b on each of control interfaces 122, typically with the thumb and forefinger, and can move the pincher assembly to various positions and orientations.

When a tool control mode is selected, the control interfaces 122 are configured to control a corresponding surgical instrument and instrument arm 106a-d. For example, a left control interface 122a may be coupled to control the instrument arm 106a and its associated surgical instrument 101a, and a right control interface 122b may be coupled to the control instrument arm 106b and its associated surgical instrument 101b. If the third instrument arm 106c is used during a surgical procedure and is positioned on the left side, then left control interface 122a can be switched from controlling the arm 106a and its associated surgical instrument 101a to controlling the arm 106c and its associated surgical instrument 101c. Likewise, if the third instrument arm 106c is used during a surgical procedure and is positioned on the right side, then the right control interface 122a can be switched from controlling the arm 106b and its associated surgical instrument 101b to controlling the arm 106c and its associated surgical instrument 101c.

In some instances, control assignments between the control interfaces 122a, 122b and combination of arm 106a/ surgical instrument and combination of arm 106b/surgical instrument may also be exchanged. This may be done, for example, if the endoscope is rolled 180 degrees, so that the instrument moving in the endoscope's field of view appears to be on the same side as the control interface the surgeon is moving.

The pincher assembly is typically used to operate a jawed surgical end effector (e.g., scissors, grasping retractor, and the like) at the distal end of a surgical instrument 101. Additional controls are provided with foot pedals 128. Each of foot pedals 128 can activate certain functionality on the selected one of instruments 101. For example, foot pedals 128 can activate a drill or a cautery tool or may operate irrigation, suction, or other functions. Multiple instruments can be activated by depressing multiple pedals 128. Certain functionality of instruments 101 may be activated by other controls. Foot petals may also be used to activate electrosurgical functionality.

The surgeon's console 120 also includes a stereo image viewer system 126 (e.g., the display system 125 shown in FIG. 1A). The stereo image viewer system 126 includes a left eyepiece 125a and a right eyepiece 125b, so that the surgeon may view left and right stereo images using the surgeon's left and right eyes respectively inside the stereo image viewer system 126. Left side and right side images captured by endoscope 112 are displayed on corresponding left and right image displays of a display system (e.g., the display system 125 shown in FIG. 1A), which the surgeon perceives as a three-dimensional image. In an advantageous configuration, the control interfaces 122 are positioned below stereo image viewer system 126 so that the images of the surgical tools shown in the display appear to be located near the surgeon's hands below the display. This feature allows the surgeon to intuitively control the various surgical instruments in the three-dimensional display as if watching the hands directly. Accordingly, the servo control of the associated instrument arm and instrument is based on the endoscopic image reference frame.

The endoscopic image reference frame is also used if the control interfaces 122 are switched to a camera control mode. In some cases, if the camera control mode is selected, the surgeon may move the distal end of an endoscope by moving one or both of the control interfaces 122 together. The surgeon may then intuitively move (e.g., pan, tilt, zoom) the displayed stereoscopic image by moving the control interfaces 122 as if holding the image in his or her hands.

As is further shown in FIG. 1C, a headrest 130 is positioned above stereo image viewer system 126. As the surgeon is looking through stereo image viewer system 126, the surgeon's forehead is positioned against headrest 130. In some embodiments of the present disclosure, manipulation of endoscope 112 or other surgical instruments can be achieved through manipulation of headrest 130 instead of utilization of the control interfaces 122.

Figure 1D:
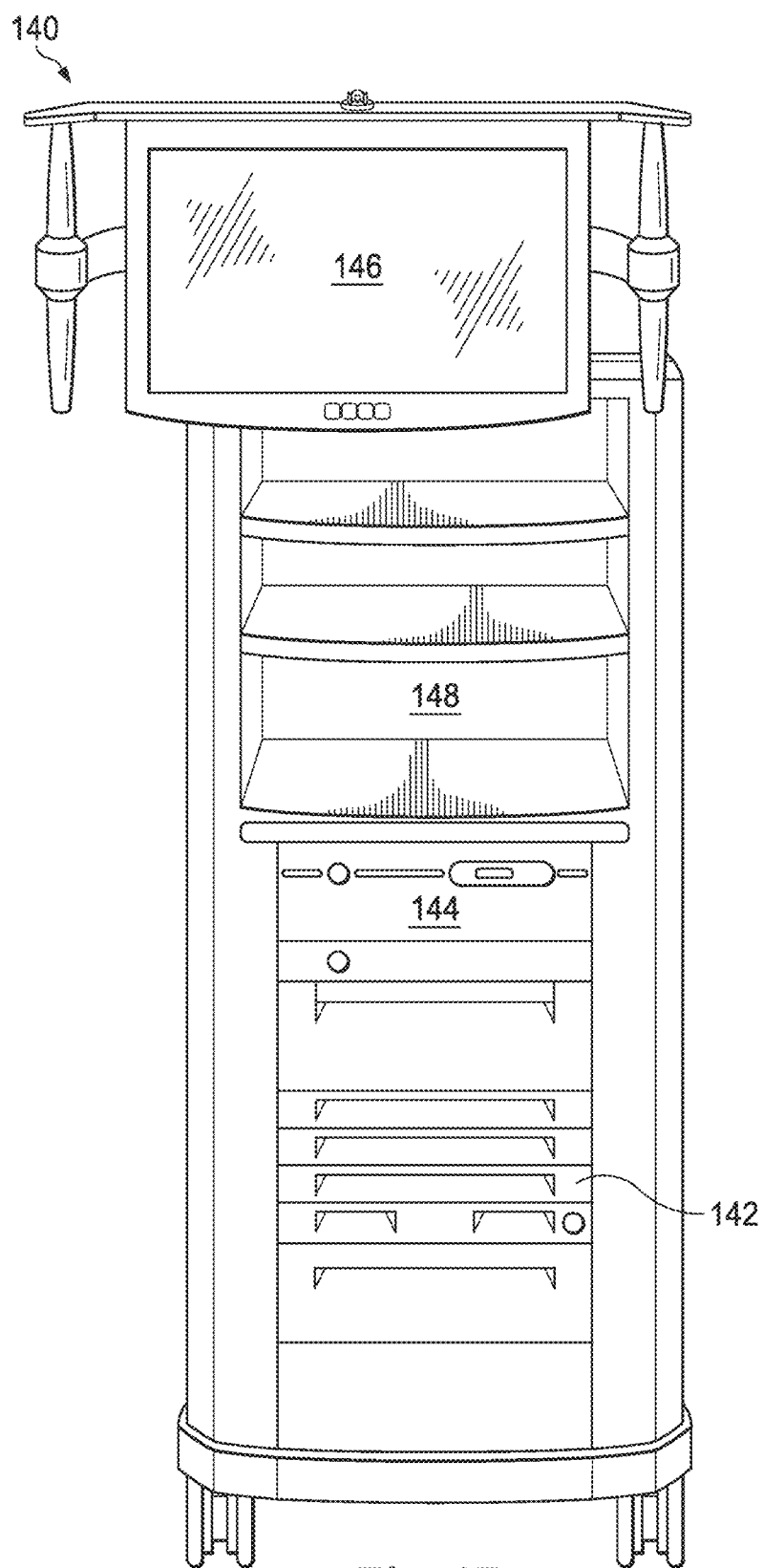
FIG. 1D illustrates a front view of an exemplary vision cart component according to one embodiment of the present disclosure.

FIG. 1D is a front view of a vision cart component 140 of a surgical system. For example, in one embodiment, the vision cart component 140 is part of the medical system 100 shown in FIG. 1A. The vision cart 140 can house the surgical system's central electronic data processing unit 142 (e.g., all or portions of vision cart 140 shown in FIG. 1A) and vision equipment 144 (e.g., portions of the image capture system). The central electronic data processing unit 142 includes much of the data processing used to operate the surgical system. In various implementations, however, the electronic data processing may be distributed in the surgeon console 120 and teleoperational assembly 115. The vision equipment 144 may include camera control units for the left and right image capture functions of the endoscope 112. The vision equipment 144 may also include illumination equipment (e.g., a Xenon lamp) that provides illumination for imaging the surgical site.

As shown in FIG. 1D, the vision cart 140 includes an optional touchscreen monitor 146 (for example a 24-inch monitor), which may be mounted elsewhere, such as on the assembly 115 or on a patient side cart. The vision cart 140 further includes space 148 for optional auxiliary surgical equipment, such as electrosurgical units, insufflators, suction irrigation instruments, or third-party cautery equipment. The teleoperational assembly 115 and the surgeon's console 120 are coupled, for example, via optical fiber communications links to the vision cart 140 so that the three components together act as a single teleoperated minimally invasive surgical system that provides an intuitive telepresence for the surgeon.

Figure 1E:
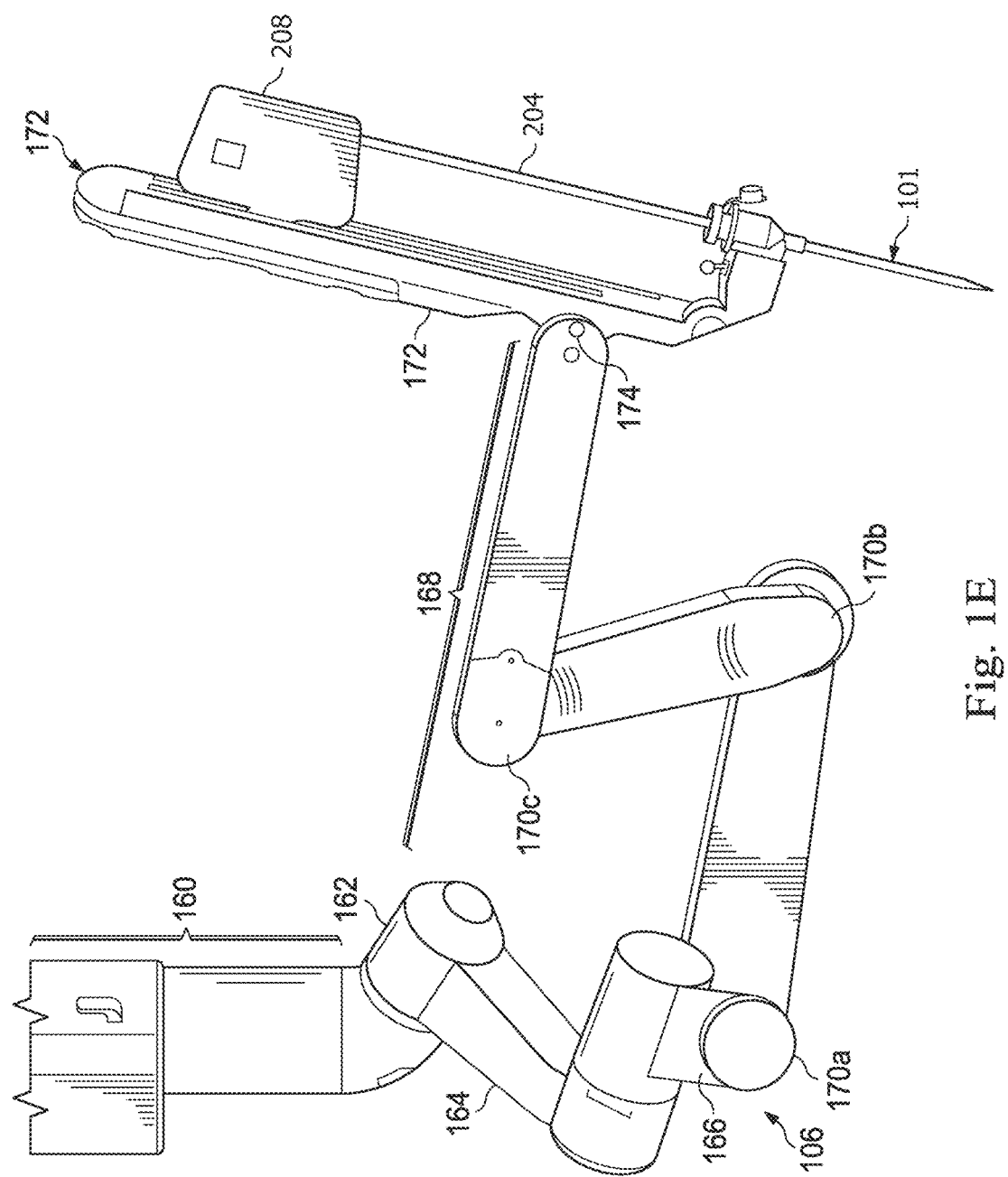
FIG. 1E illustrates an arm of the exemplary teleoperational assembly of FIG. 1B according to one embodiment of the present disclosure.

FIG. 1E shows one of the arms 106 with an interchangeable surgical instrument 101 mounted thereon. The surgical instrument 101 may be an endoscope mounted on the arm 106 designated as the camera arm. The endoscope may be a stereo endoscope for capturing stereo images of the surgical site and providing the separate stereo images to the display system 125. Knowledgeable persons will appreciate that the arms that support the instruments and the camera may also be supported by a base platform (fixed or moveable) mounted to a ceiling or wall, or in some instances to another piece of equipment in the operating room (e.g., the operating table). Likewise, they it can be appreciated that two or more separate bases may be used (e.g., one base supporting each arm).

As is further illustrated in FIG. 1E, the instrument 101 includes an instrument interface base 208 and an instrument shaft 204. In some embodiments, the teleoperational assembly 115 may include supports for cannulas that fix the instrument 101 with respect to the cannulas. In some embodiments, portions of each of the instrument arms 106 may be adjustable by personnel in the operating room in order to position the instrument with respect to a patient. Other portions of the arm 106 may be actuated and controlled by the operator at an operator input system 120 (as shown in Figure 1C). The surgical instrument 101 associated with each arm 106 may also be controlled by the operator at the operator input system 120.

The surgical tools 101 are generally sterile structures, often being sterilizable and/or being provided in hermetically sealed packages for use. As the teleoperated surgical tools 101 will be removed and replaced repeatedly during many procedures, a tool holder could potentially be exposed to contamination if the interface directly engages the tool holder. To avoid contamination to a tool holder and possible cross contamination between patients, an adaptor for coupling to teleoperated surgical tools 101 is provided in a teleoperated arm of the teleoperated surgical manipulator.

In more detail, the arm 106 includes a vertical setup 160 connected via a setup joint 162 to a distal-most setup link 164. A yaw joint 166 connects the distal-most setup link 162 to a parallelogram pitch mechanism 168. The parallelogram pitch mechanism 164 includes a plurality of pitch joints 170a, 170b, 170c enabling it move. A spar 172 connects to the parallelogram pitch mechanism 164 at a spar joint 174. Each of the setup joint 162, the yaw joint 166, the pitch joints 170a, 170b, 170c, and the spar joint 174 are controlled by motors, referenced herein as a setup joint motor, a yaw joint motor, pitch joint motors, and a spar joint motor. Accordingly, the arm 106 is configured to move in a motorized fashion. In this embodiment, the motors are under the control of the vision cart 140 and may be operated with motors of the other arms to take desired poses that may assist with draping, advancing over a patient, docking to surgical instruments, or storage, among others. In addition, encoders and sensors associated with each motor provide feedback to the vision cart 140 so that the control system senses or detects the position, status, and setup of the arm 106. In some embodiments, the spars 172 include sensors to detect the presence of surgical drapes on the arms 106.

The teleoperational assembly 115 also includes a helm 111 fixed relative to the base 102 on the support column 104 with a user interface for controlling the setup and operation. In some embodiments, the user interface is a touchpad 154 capable of accepting user inputs and providing graphical, textual, auditory, or other feedback. The touchpad 154 provides features for teleoperational assembly 115 activities such as preparation for draping, docking, or stowing to help the user minimize the space it takes up in the OR. The touchpad 154 also provides a means for system fault notification and recovery. In some embodiments, the touchpad 154 is disposed along the support column 104 and is configured to be viewed by a user in the operating room. In other embodiments, the touchpad or other user interface is disposed elsewhere. It may be wired or wireless and may be disposed within bag or elsewhere for sterile use. The touchpad 154 in this embodiment is configured to display informational data relating to status of the teleoperational assembly 115, information relating to particular surgical procedures, and information relating to the overall teleoperational medical system 100. In some embodiments, the touchpad 154 is a touchpad display interface that presents information and accepts user inputs. As such, a user may input control instructions, including setup instructions, at the touchpad.

Teleoperated Electrosurgical Tool

Figure 2A:
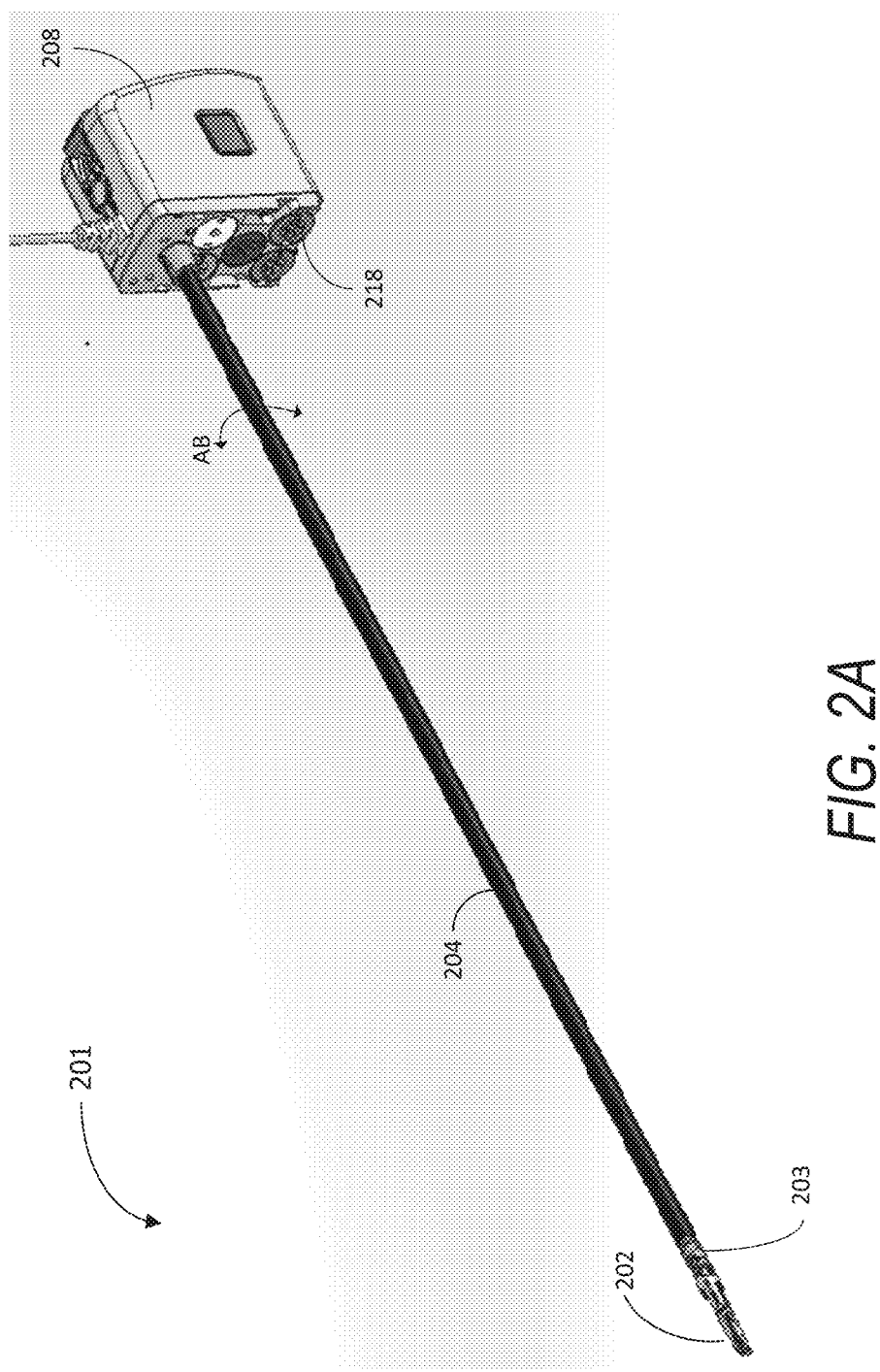
FIGS. 2A-2D illustrates an exemplary teleoperated surgical tool disclosed herein according to embodiments of the present disclosure.

Referring now to the FIG. 2A, a perspective view of an exemplary embodiment of a teleoperated electrosurgical tool 201 is shown. The electrosurgical tool 201 generally has four main sections including a mountable housing 208, a hollow shaft 204, a wrist 203, and an end effector 202. Embodiments of the invention are described including wrist 203, however the end effector 202 may also be mounted directly to hollow shaft 204 in a fixed configuration.

The mountable housing 208 mounts onto an adapter 228 on the teleoperated surgical arm 106. Rotatable receiving members 218 on the mountable housing 208 mechanically couple to rotatable drivers 234 on the teleoperated surgical arm 106. Rotation of the rotatable drivers 234, rotate the rotatable receiving members 218 which in turn actuate rods and/or cables in the shaft 204 to actuate the wrist 203 and/or end effectors 202. A more detailed explanation of the electrosurgical tool 201 is given below with reference to FIGS. 2B-2D illustrating different views of a mountable housing 208, operationally similar to the mountable housing 208 of FIG. 2A, and adapter 228 of the teleoperated surgical arm 106.

Figure 2D:
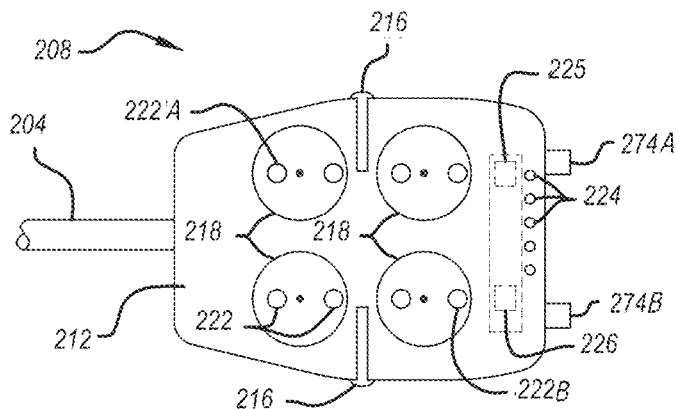
Figure 2C:
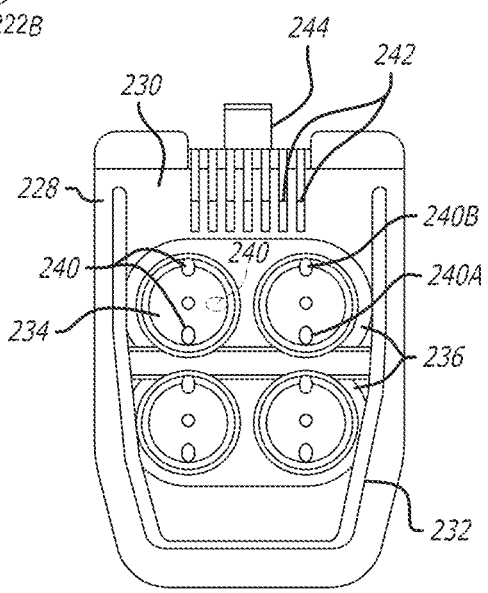
Figure 2B:
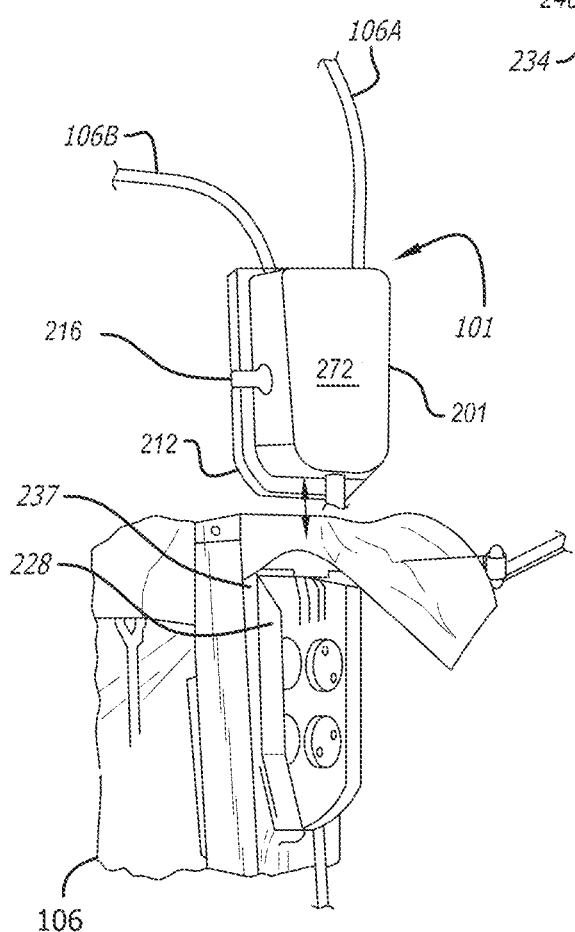

Referring now to FIGS. 2B-2D, the mounting of the electrosurgical tool 201 to an adapter 228 of the teleoperated surgical arm is now briefly described. The teleoperated surgical arm 106 may include an adapter 228 to which the electrosurgical tool 201 or other surgical tool 101 may be mounted. FIG. 2C illustrates a front side of an exemplary adapter 228. The front side of the adaptor 228 is generally referred to as a tool side 230 and the opposite side is generally referred to as a holder side (not shown).

FIG. 2D illustrates a back side of an exemplary electrosurgical tool 201. The electrosurgical tool 201 includes an exemplary mountable housing 208 including an interface base 212 that can be coupled to the adapter 228 to mount the electrosurgical tool 201 to a teleoperated arm of a teleoperated surgical manipulator. The interface base 212 and the adapter 228 may be electrically and mechanically coupled together to actuate the electrosurgical tool 201. Rotatably coupled to the interface base 212 are one or more rotatable receiving members 218, also referred to as input disks. Each of the one or more rotatable receiving members 218 includes a pair of pins 222A and 222B generally referred to as pins 222. Pin 222A is located closer to the center of each rotatable receive member 218 than pin 222B. The one or more rotatable receiving members 218 can mechanically couple respectively to one or more rotatable drivers 234 of the adapter 228. The electrosurgical tool 201 may further include release levers 216 to release it from the adapter 228 and the teleoperated arm.

The interface base 212 may further include one or more electrical contacts or pins 224 to electrically couple to terminals of an electrical connector 242 of the adapter 228. The interface base 212 may further include a printed circuit board 225 and one or more integrated circuits 226 coupled thereto and to the one or more pins 224. The one or more integrated circuits 226 store tool information that may be used to identify the type of teleoperated surgical tool coupled to the teleoperated arm, so that it may be properly controlled by the operator input system 120.

Referring to FIGS. 2B and 2D, an electrosurgical tool or instrument 101 is illustrated. The electrosurgical tool 201 includes a mountable housing 208, an elongated shaft 204 having a proximal end and a distal end; and end effectors (not shown) coupled near the distal end of the shaft 204. The mountable housing 208 includes an interface or tool base 212 coupled to the proximal end of the shaft 204. The mountable housing 208 may further include one or more electrical connectors 274A-274B, a cover 272, and one or more release levers 216. At the distal end of the shaft 204, a mechanical wrist (not shown) may be used to move the end effectors.

One or more cables 106A-106B may be respectively coupled to one or more connectors 274A-274B of the electrosurgical tool 101 to make electrocautery connections, such as between an integrated electrosurgical controller and the tool and/or between the tool and an electrosurgical generating unit.

The interface or tool base 212 of the electrosurgical tool 201 can couple to an adapter 228 so that it is removeably connectable to the teleoperated surgical system. Other surgical tools with the same type of tool base may also couple to the adapter and on the teleoperated arm. During surgery, the adapter 228 is coupled to the moveable carriage 237. Thus, with the electrosurgical tool 201 mounted to the adapter 228, it can translate with the carriage 237 along an insertion axis of the teleoperated surgical arm 106. The tool base 212 includes receiving elements or input disks 218 that releaseably couple through the adapter 228 to a rotatable driving element 234 that is mounted on the carriage 237 of the teleoperated arm assembly 106. The rotatable driving elements 234 of the carriage 237 are generally coupled to actuators (not shown), such as electric motors or the like, to cause selective angular displacement of each in the carriage 237.

When mounted to a teleoperated surgical arm 106, end effectors 202 may have a plurality of degrees of freedom of movement relative to arm 106, in addition to actuation movement of the end effectors. The end effectors of the teleoperated surgical tool are used in performing a surgical operation such as cutting, shearing, grasping, gripping, clamping, engaging, or contacting tissue adjacent a surgical site. With an electrosurgical tool 201, a conductor electrically communicates with the end effector to deliver electrical energy to tissue clamped by the gripping jaws or otherwise in contact with the end effector.

As shown in FIG. 2D, the tool base 212 may be enclosed by a cover 272 to which one or more electrical connectors 274A-274B may be mounted. The one or more electrical connectors 274A-274B can receive one or more cables 108A-108B to couple to an electrosurgical generator unit, such as the bipolar generator 110B, the monopolar generator 110A, or a monopolar/bipolar generator 110A/110B illustrated in FIG. 1A. One or more wires within the tools electrically couple between the electrical connectors 274A-274B and the one or more electrodes at the end effector of the tool.

The adapter 228 includes one or more rotatable drivers 234 rotatably coupled to a floating plate 236. The rotatable drivers 234 are resiliently mounted to the floating plate 236 by resilient radial members which extend into a circumferential indentation about the rotatable drivers. The rotatable drivers 234 can move axially relative to floating plate 236 by deflection of these resilient structures.

The floating plate 236 has a limited range of movement relative to the surrounding adaptor structure normal to the major surfaces of the adaptor. Axial movement of the floating plate helps decouple the rotatable drivers 234 from an electrosurgical tool 201 when its release levers 216 are actuated.

The one or more rotatable drivers 234 of the adapter 228 may mechanically couple to a part of the surgical tools 101. Each of the rotatable drivers 234 may include one or more openings 240 to receive protrusions or pins 222 of rotatable receiving members 218 of the surgical tools 101. The openings 240 in the rotatable drivers 234 are configured to accurately align with the rotatable receiving elements 218 of the surgical tools 101. In other embodiments of the invention, pins 222 and rotatable receiving members 218 may be swapped. In such embodiments, the pins 222 would be on the rotatable drivers 234 and the openings 240 would be on rotatable receiving members 218.

The inner pins 222A and the outer pins 222B of the rotatable receiving elements 218 respectively align with the opening 240A and the opening 240B in each rotatable driver. The pins 222A and openings 240A are at differing distances from the axis of rotation than the pins 222B and openings 240B so as to ensure that rotatable drivers 234 and the rotatable receiving elements 218 are not aligned 180 degrees out of phase from their intended position. Additionally, each of the openings 240 in the rotatable drivers may be slightly radially elongated so as to fittingly receive the pins in the circumferential orientation. This allows the pins 222 to slide radially within the openings 240 and accommodate some axial misalignment between the tool and the adapter 228, while minimizing any angular misalignment and backlash between the rotatable drivers 234 and the rotatable receiving elements 218. Additionally, the interaction between pins 222 and openings 240 helps restrain the electrosurgical tool 201 in the engaged position with the adapter 228 until the release levers 416 along the sides of the housing 208 push on the floating plate 236 axially from the interface so as to release the surgical tool 101.

When disposed in a first axial position (away from the tool side 230) the rotatable drivers are free to rotate without angular limitation. The one or more rotatable drivers 234 may rotate clockwise or counter-clockwise to further actuate the systems and tools of the teleoperated surgical instruments 101. However, as the rotatable drivers move axially toward the tool side 230, tabs (extending radially from the rotatable drivers) may laterally engage detents on the floating plates so as to limit the angular rotation of the rotatable drivers about their axes. This limited rotation can be used to help engage the rotatable drivers the rotating members of the tool as the pins 222 may push the rotatable bodies into the limited rotation position until the pins are aligned with (and slide into) the openings 240 in the rotatable drivers.

While rotatable drivers 234 are described here, other types of drivers or actuators may be provided in the adapter 228 to actuate systems or tools of the teleoperated surgical instruments 101. The adapter 228 further includes terminals of an electrical connector 242 to couple to electrical contacts or pins 424 of surgical instruments 101 to make an electrical connection as well.

The mounting of electrosurgical tool 201 to the adapter 228 generally includes inserting the tip or distal end of the shaft or hollow tube of the teleoperated surgical tool through a cannula (not shown) and sliding the interface base 212 into engagement with the adapter 228, as illustrated in FIG. 2C. A lip 232 on the tool side 230 of the adaptor 228 slideably receives the laterally extending portions of the interface base 212 of the teleoperated surgical tool. A catch 244 of adapter 228 may latch onto the back end of the interface base 212 to hold the tool 101 in position. The protrusions or pins 222 extending from the one or more rotatable receiving elements 218 of the teleoperated surgical tool couple into the holes 240A-240B (generally referred to as holes or openings 240) in the rotatable drivers 234 of the adapter 228.

The range of motion of the rotatable receiving elements 218 in the teleoperated surgical tool may be limited. To complete the mechanical coupling between the rotatable drivers of the adapter and the rotatable receiving elements 218, the operator O at the surgical operator input system 120 may turn the rotatable drivers in one direction from center, turn the rotatable drivers in a second direction opposite the first, and then return the rotatable drivers to center. Further, to ensure that the pins 222 enter openings 240 of rotatable drivers adapter 228, the adapter 228 and tool 101 mounted thereto may be moved together. The adapter 228 and tool 101 mounted thereto may be moved to an initial position so that the tip or distal end of the shaft or hollow tube is disposed within a cannula (not shown).

To dismount and remove the electrosurgical tool 201, the release levers 216 may be squeezed pushing out on the mountable housing 208 to release the pins 222 from the holes 240 and the catch 244 from the back end of the interface base. The mountable housing 208 is then pulled up to slide the interface base 212 up and out from the adapter 228. The mountable housing 208 is continually pulled up to remove the tip or distal end of the shaft or hollow tube out from the cannula 219. After the electrosurgical tool 201 is dismounted, another teleoperated surgical tool may be mounted in its place, including a new or freshly sterilized electrosurgical tool 201.

As previously discussed, the electrosurgical tool 201 may include one or more integrated circuits 226 to identify the type of teleoperated surgical tool coupled to the teleoperated arm, such that it may be properly controlled by the operator input system 120. However, the teleoperated surgical system may determine whether or not the teleoperated surgical tool is compatible or not, prior to its use.

The system verifies that the tool is of the type which may be used with the teleoperated surgical system 115. The one or more integrated circuits 226 may signal to the computer 151 in the operator input system 120 data regarding compatibility and tool-type to determine compatibility as well as control information. One of the integrated circuits 226 may include a non-volatile memory to store and read out data regarding system compatibility, the tool-type and the control information. In an exemplary embodiment, the data read from the memory includes a character string indicating tool compatibility with the teleoperated surgical system 115. Additionally, the data from the tool memory will often include a tool-type to signal to the operator input system how it is to be controlled. In some cases, the data will also include tool calibration information. The data may be provided in response to a request signal from the computer 151.

Tool-type data will generally indicate what kind of tool has been attached in a tool change operation. The tool-type data may include information on wrist axis geometries, tool strengths, grip force, the range of motion of each joint, singularities in the joint motion space, the maximum force to be applied via the rotatable receiving elements, the tool transmission system characteristics including information regarding the coupling of rotatable receiving elements to actuation or articulation of a system within the teleoperated surgical instrument.

For example, the tool-type data might indicate that an electrosurgical instrument 101 has been mounted to the teleoperated arm or not. Relevant to energy activation of an electrosurgical instrument, additional tool type data related to primary and/or secondary energy sub-features may further be stored. For example, energy sub-features may include what type of electrosurgical energy the tool may receive (e.g., bipolar or monopolar cutting & monopolar coagulating), maximum peak energy, minimum harmonic energy frequency, maximum harmonic energy frequency, and whether or not a laser is also provided for cutting. As new energy or other types of modalities are introduced for teleoperated surgical tools, its tool-type data can be readily stored and communicated to the teleoperated surgical system so that the system can adaptively control remote controllable equipment and multiple types of teleoperated surgical tools mounted to teleoperated arms of the teleoperated surgical system.

Instead of storing all of the tool-type data in the one or more integrated circuits 426, most of the tool-type data may optionally be stored in memory or a hard drive of the computer 151 in the teleoperated surgical system 115. An identifier may be stored in the one or more integrated circuits 226 to signal the computer 151 to read the relevant portions of data in a look up table store in the memory or the hard drive of the computer. The tool-type data in the look-up table may be loaded into a memory of computer 151 by the manufacturer of the teleoperated surgical system 115. The look-up table may be stored in a flash memory, EEPROM, or other type of non-volatile memory. As a new tool-type is provided, the manufacturer can revise the look-up table to accommodate the new tool-specific information. It should be recognized that the use of tools which are not compatible with the teleoperated surgery system, for example, which do not have the appropriate tool-type data in an information table, could result in inadequate control over the teleoperated surgical tool by the computer 151 and the operator O.

In addition to the tool-type data, tool specific information may be stored in the integrated circuit 226, such as for reconfiguring the programming of computer 151 to control the tool. There may be calibration information, such an offset, to correct a misalignment in the teleoperated surgical tool. The calibration information may be factored into the overall control of the teleoperated surgical tool. The storing of such calibration information can be used to overcome minor mechanical inconsistencies between tools of a single type. For example, the tool-type data including the tool-specific data may be used to generate appropriate coordinate transformations and servo drive signals to manipulate the teleoperated arm and rotate the rotatable drivers 234. In this case, the integrated circuit 226 includes the information to set up the control system to drive the end effectors in the tool to have a maximum joint torque setting so that the jaws of a robotic gripping tool or a electrosurgical tool can clamp to tissue with a maximum force.

Additionally, some teleoperated surgical tools have a limited life span. Tool life and cumulative tool use information may also be stored on the tool memory and used by the computer to determine if the tool is still safe for use. Total tool life may be measured by clock time, by procedure, by the number of times the tool has been loaded onto a holder, and in other ways specific to the type of tool. Tool life data is preferably stored in the memory of the tool using an irreversible writing process.

Electrosurgical End Effector

At the distal end of the electrosurgical tool 201 is a surgical end effector 202. The surgical end effector 202 may be one, or in some cases a combination, of a variety of surgical tools including, tissue graspers, scissors, cauterizers, etc. An exemplary surgical end effector illustrated in FIGS. 5A-8B is an electrosurgical end effector. Embodiments of the surgical end effector illustrated in FIG. 5A-8B is a tissue sealer/cauterizer with an otomy feature. Other types of surgical end effectors may be at the distal end of the electrosurgical tool 201 such as a surgical grasper with a similar otomy feature.

Briefly referring back to referring now to FIG. 2A, a surgical instrument 101 for use with the minimally invasive teleoperated surgical system of FIG. 1 comprises an elongate shaft 404 having a proximal end and a distal end. An interface or tool base 212 is coupled to the proximal end of the shaft and removably connectable to the teleoperated surgical system. The interface base 212 includes receiving members 218 to couple to drivers 234 on the teleoperated arm 106. An end effector 202, for performing a surgical operation such as cutting, shearing, sealing, grasping, engaging, or contacting tissue in a surgical site, is mounted at the distal end of the shaft. The drivers 234 provide actuating force to move the end effector 202. The end effector 202 includes a pair of jaws for cooperatively grasping, sealing, and/or shearing tissue. A conductor electrically communicating with at least one jaw delivers electrical energy to tissue engaged by the jaws or contacting the jaw(s).

At the distal end of the shaft 204 is a mechanical wrist 203 to move the end effectors 202. The interface or tool base 212 can couple to an adapter 228 to which other surgical tools may also couple so that the electrosurgical tool 201 is removably connectable to the teleoperated surgical system. The adapter 228 is coupled to an actuating portion of the teleoperated surgical arm 106. One or more rotatable receiving members 218 on the electrosurgical tool 201 mechanically couple to one or more rotatable drivers 234 of the adapter 228.

When mounted to a teleoperated surgical arm 106, end effectors 202 may have a plurality of degrees of freedom of movement relative to arm 106, in addition to actuation of the end effectors 202. Degrees of freedom of the electrosurgical tool 201 may be provided by an articulating wrist 203 between the shaft 204 and end effector 202. The elongated shaft 204 is rotatably mounted to the base 212 for rotation about an axis extending longitudinally along the shaft 204 as indicated by the rotational arrow AB.

The wrist 203 may be a single pivot wrist, a multi-pivot wrist, a distal roll joint mechanism, or other joints or wrist-like mechanism to provide additional operational degrees of freedom to the end effector. The orientation of the mechanical wrist 203 is controlled through pulleys in the tool base 212 and the wrist 203 with cables of cable loops wrapped around each pulley being routed through the shaft 204. The teleoperated system causes the pulleys in the tool base 212 to be rotated in order to control the position of the mechanical wrist 203. Thus, the cable of the cable loops may also be referred to as a control cable.

Further details of mechanical wrists that may be applicable to the mechanical wrist 203 are described in U.S. Patents with filing dates and named inventor as follows U.S. Pat. No. 5,792,135, May 16, 1997, Madhani et al; U.S. Pat. No. 5,979,900, May 16, 1997, Madhani et al; U.S. Pat. No. 5,807,377, May 16, 1997, Madhani et al; U.S. Pat. No. 6,206,903, Oct. 8, 1999, Ramans; U.S. Pat. No. 6,312,435, Oct. 8, 1999, Wallace et al.; U.S. Pat. No. 6,371,952, Jun. 28, 1999, Madhani et al; U.S. Pat. No. 6,394,998, Sep. 17, 1999, Wallace et al.; U.S. Pat. No. 6,676,684, Sep. 4, 2001, Morley et al.; U.S. Pat. No. 6,685,698, Jan. 10, 2003, Morley et al.; U.S. Pat. No. 6,699,235, Mar. 2, 2004, Wallace et al.; U.S. Pat. No. 6,746,443, Jul. 27, 2000, Morley et al.; and U.S. Pat. No. 6,817,974, Jun. 28, 2002, Cooper et al., all of which are incorporated herein by reference. Embodiments of the invention are described including wrist 203, however the end effector 202 may also be mounted directly to hollow shaft 204 in a fixed configuration.

Figure 3:
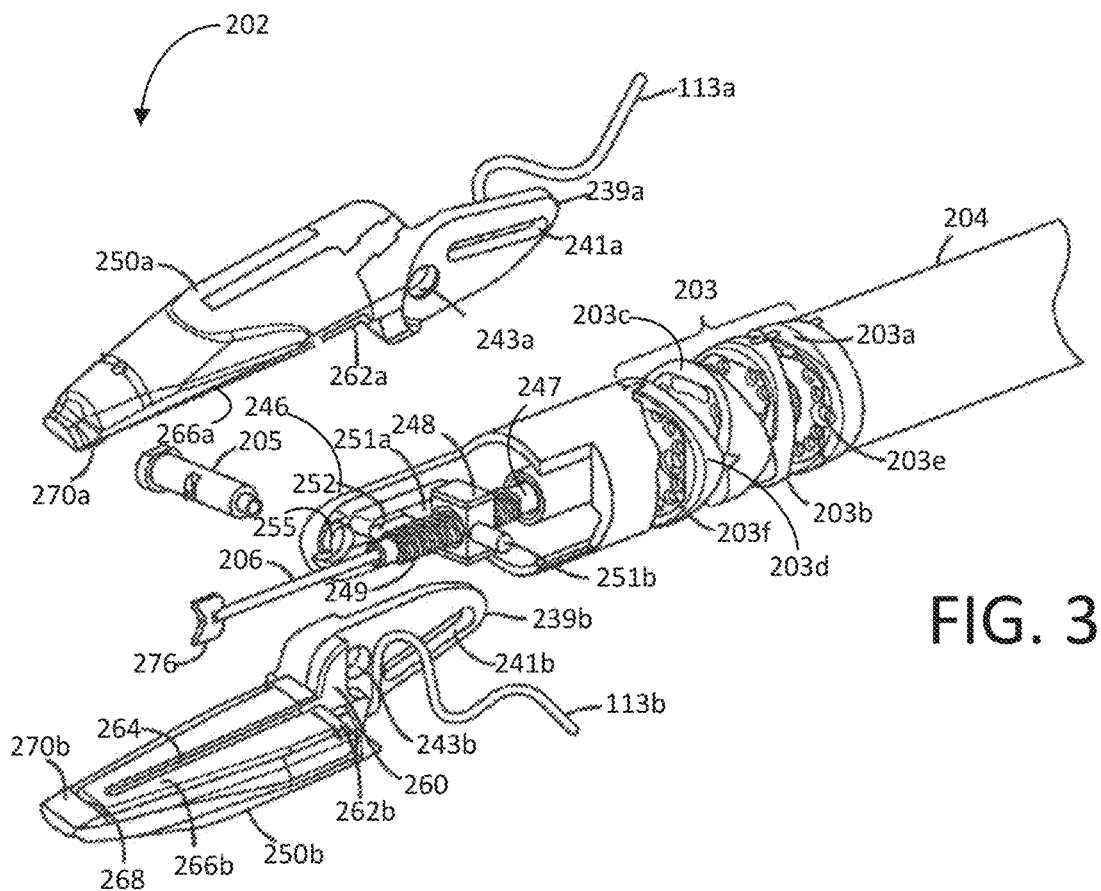
FIG. 3 illustrates an exemplary teleoperational surgical tool in a frontal perspective view according to embodiments of the present disclosure.

Referring now to FIG. 3, a partially exploded view of an exemplary end effector 202 is shown. FIG. 3 illustrates one exemplary method of actuating a jaw of an end effector 202 with a rotatable mechanism. Further details of the rotatable mechanism are disclosed in U.S. Pat. App. Pub. No. 2012/0150154 titled DECOUPLING INSTRUMENT SHAFT ROLL AND END EFFECTOR ACTUATION IN A SURGICAL INSTRUMENT, filed by Gabriel F. Brisson and William Burbank on Nov. 15, 2011, incorporated herein by reference. FIG. 3 also illustrates one exemplary method of actuating a mechanical knife or a retractable otomy feature with a push-pull mechanism. Further details of the push-pull mechanism are disclosed in U.S. Pat. No. 9,055,961 titled FUSING AN CUTTING SURGICAL INSTRUMENT AND RELATED METHODS, filed by Scott E. Manzo and Lawrence Kerver on Feb. 17, 2012, incorporated herein by reference.

In FIG. 3, an exploded view of an end effector 202 coupled to a mechanical wrist 203 of a tool is shown. The end effector 202 includes one or more jaws 250a,205b pivotally coupled to a clevis 246 of the end effector body. The upper jaw 250a has a tissue portion and a cam portion 239a with an angled cam slot 241a and a pivot hole 243a. An insulated electrical conductor (wire) 113a is coupled to the jaw 250a. The lower jaw 250b has a tissue portion and a cam portion 239b with an angled cam slot 241b and a pivot hole 243b. An insulated electrical conductor (wire) 113b is coupled to the jaw 250b. One or more electrical conductors 113a,113b may be electrically coupled to a generator such as monopolar generator 110A shown in FIG. 1A. The one or more electrical conductors provide electrical energy to the end effector 202 for sealing, cutting, cauterizing, otomy, etc. A coupling pin 205 is inserted into opposing openings 255 (only one shown) and openings 243a-243b to pivotally couple the one or more jaws 250a,250b to the clevis 246 (only one side shown in FIG. 3) of the end effector body. The pin 205 provides a pivot point for one or both jaws. In some embodiments, the lower jaw 250b may be fixed as a part of the drive body extending from the clevis.

The tool 202 further includes a shaft 204 coupled to a wrist 203. The wrist 203 includes individual wrist plates 203a-203d with a plurality of various through holes 203e-203f. Wrist 203 and wrist plates 203a-203d allow the end effector 202 multiple degrees of freedom. Channel tendon cables are routed through holes 203e-203f to actuate the wrist plates. Other holes in the wrist plates provide pathways for optical fibers for light, video, and electrical conductors 113, etc., to the end effector 202 without interfering with the degrees of freedom of the end effector 202.

Adjacent the wrist, the end effector body further includes a threaded drive nut 248 with an internal thread pivotally coupled to an external threaded sleeve 249 of a hollow drive shaft 247. The drive nut 248 includes drive protrusions 251a-251b that are slidingly coupled into opposing drive slots 252 (only one side shown) of the clevis 246 and the angled slots 241a-241b of the jaws. The drive protrusions 251a-251b are pulled in and pushed out from the clevis 246 by the rotation of the drive shaft 247 coupled to the threaded sleeve 249.

The exemplary embodiment illustrated in FIG. 3 also discloses other features that may or may not be present in other embodiments of the invention. For example, a sealing feature is disclosed in FIG. 3. A horseshoe shaped tissue seal electrode 266b is disposed on the jaw surface of jaw 250b. As shown, the seal electrode 266b includes a blade channel 264 bisecting the seal electrodes 266b to guide mechanical knife blade 276. The blade channel 264 is configured to receive and provide a track for the knife blade 276 as it translates in the proximal and distal directions relative to the jaws 250a,250b.

In a closed position of the jaws 250a, 250b, seal electrodes 266b is maintained spaced apart from opposite seal electrode 266a on jaw 250a, by spacer lips 270a, 270b disposed at the distal ends of jaw 250a, 250b, and by spacer bar 262a, 262b at a proximal end of the seal electrodes 266a, 266b. The height of the spacer bars 262a, 262b above the surface of the seal electrodes 266a, 266b may be slightly lower than the height of the spacer lips 270a, 270b above the electrode surfaces to promote a uniform gap g across the length of the electrode surfaces while also permitting the electrode surfaces to come sufficiently close along their entire length to ensure effective gripping and sealing of tissue.

Figure 4:
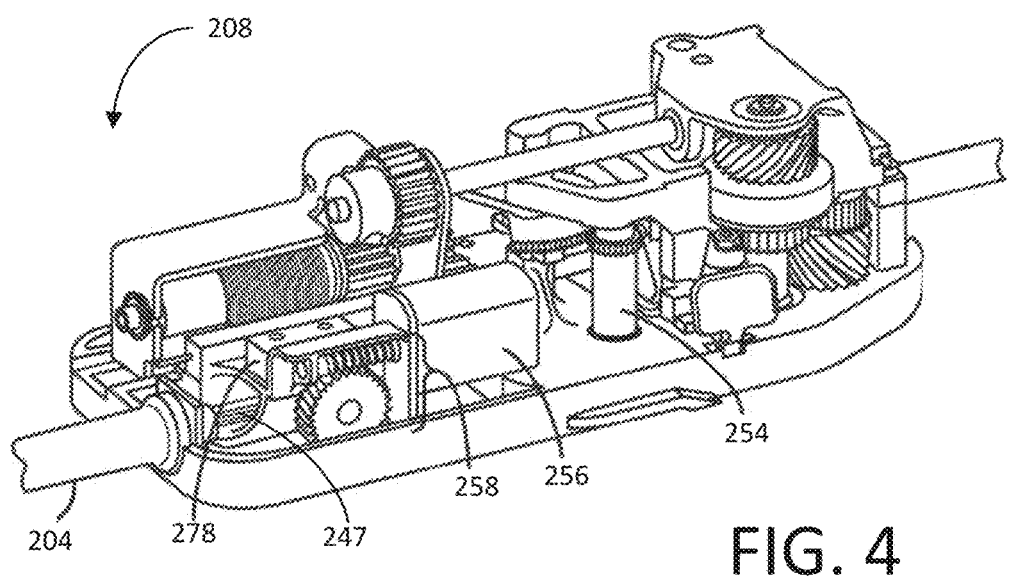
FIG. 4 illustrates the exemplary back end or mountable housing of a teleoperational surgical tool according to embodiments of the present disclosure.

Referring now to FIG. 4, a side perspective view of an exemplary mountable housing 208 is shown without a cover. The mountable housing 208 includes a drive shaft 254, an internal electric drive motor 256, and a rack and pinion transmission 258. To control the movement of the mechanical knife 276, one or more limit switches 278 can be used to sense the position of the mechanical knife 276. For one exemplary embodiment of using a limit switch to sense the position and assist in controlling the operation of the mechanical knife, reference is made to U.S. Provisional Patent Application No. 61/491,698, entitled "SURGICAL INSTRUMENT WITH MOTOR" (filed May 31, 2011) and to U.S. Provisional Patent Application No. 61/491,671, entitled "SURGICAL INSTRUMENT WITH CONTROL FOR DETECTED FAULT CONDITION" (filed May 31, 2011), both incorporated by reference herein. The drive shaft 254 may be coupled to a receiving member 218 to actuate tendon cables routed through the shaft 204 to the wrist 203 to control its movement.

Referring back to FIG. 3, a rotating motion of the hollow drive shaft 247 is used to actuate the one or more jaws 250a-250b of the end effector. The rotating movement of the drive shaft 247 causes corresponding sliding movement of the threaded drive nut 248 and its drive protrusions 251a-251b along drive slots 252. An angled cam slot 241a is disposed at a slant relative to the drive slot 252 running along the length of the clevis 246. Movement of drive protrusion 251a causes angled cam slot 241a to rotate jaw 250a about the coupling pin 205. Movement of drive protrusion 251b causes angled cam slot 241b to rotate jaw 250b about the coupling pin 205.

Referring now to FIGS. 3-4, the internal electric drive motor 256 can be coupled to the rack and pinion transmission 258 to push and/or pull on an inner drive cable coupled to the shaft 206 extending out of the drive shaft 247. Alternatively, a rotatable receiver can be coupled to the rack and pinion transmission 258 to push and/or pull on the inner drive cable coupled to the shaft 206 extending out of the drive shaft 247. Extending and retracting the shaft 206 from the sleeve 249 and the drive shaft 247 allows a mechanical knife 276 to cut tissue. Although the exemplary embodiment describes the actuation of a mechanical knife 276, the same mechanism may be used to extend and retract the otomy feature 806 shown in FIGS. 8A-8B.

Electrosurgical End Effector With Otomy Feature

FIGS. 5A-5B, 6A-6B, 7A-7B, and 8A-8B respectively provide further details of exemplary embodiments of end effectors 500,600,700,800. The end effectors illustrated in FIGS. 5A-8B are electrosurgical end effectors with a rotatable jaw and otomy feature. While the exemplary electrosurgical end effectors shown in FIGS. 5A-8B are depicted with rotatable jaws it should be understood that the otomy creating feature may be adapted to other surgical tools. Generally, the otomy feature shown in FIGS. 5A-8B is a rod shaped electrode extending from the lower jaw of the end effector. One of the advantages of the exemplary electrosurgical end effector over prior art, is the ability of the electrosurgical end effector to safely provide otomy functionality in addition to the grasping, sealing or cutting tissue function of the jawed end effector.

When performing laparoscopic surgery, tool space is limited. At times a surgeon may be controlling a surgical grasper and find that they need to create a hole in the target anatomy. Due to the limited space available, it may not be possible to introduce another surgical tool through the cannula. In such a situation, the surgeon may have to remove the surgical grasper and introduce in its place an otomy tool. While possible, such a maneuver is time consuming. To solve this problem, the otomy creating feature of the invention is incorporated into the surgical jawed end effector.

Prior art electrosurgical energy instruments such as hooks, spatulas, and monopolar curved scissors are generally electrically active during normal use. This may lead to unintended consequences if the energy instrument accidently contacts non-target tissue. Some embodiments of the invention, address this problem by decoupling the otomy feature from the electrosurgical generator during normal use of the instrument, when the otomy feature is unused.

Figure 5A:
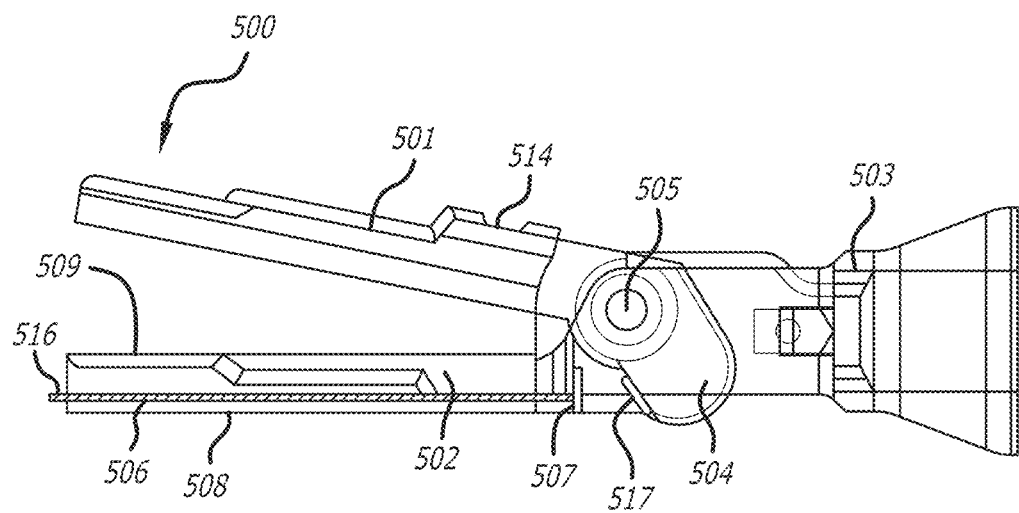
FIGS. 5A-5B illustrate an exemplary end effector of a surgical tool with otomy feature used in a teleoperational assembly such as one shown in FIG. 1B.

With reference to FIG. 5A, a side view of an exemplary embodiment of electrosurgical end effector 202. In this embodiment, end effector 500 (similar to end effector 202 of FIG. 2A) is a jawed end effector with an otomy feature 506. As with end effector 202, the end effector 500 is attached to a wrist component 503 (wrist 203 shown in FIG. 2A). The wrist component allows for a plurality of degrees of freedom. The exemplary end effector 500 is a tissue grasper; however it should be understood that other surgical instruments, such as a tissue sealer, may also benefit from the inventive concepts disclosed herein. For example, in some embodiments of the invention, inner jaw surface 509 may be conductive, and when energized, would function as a sealing/cauterizing electrode. Alternatively, inner jaw surface 509 may include one or more electrodes for sealing, desiccating, or cauterizing vessels and tissue.

The end effector 500 includes a pivotal jaw 501 and a fixed jaw 502. The pivotal jaw 501 includes a working portion 514 and an angled or bent cam portion 504. The bent cam portion 504 is separated from the working portion by a pivotal opening. The bent cam portion 504 includes a conductive contact surface 517 along its outer edge. The conductive contact surface 517 may be electrically active regardless of operational mode. The conductive contact surface 517 may be hidden by the jaw to prevent it from touching the patient and damaging tissue. The conductive contact surface 517 may be insulated from other portions of the jaw 501 so that it avoids damaging tissue, those portions may touch, when the contact surface 517 is energized. To further reduce the likelihood of accidental unwanted discharge of electrical energy, outer surfaces of the pivotal jaw 501 may be insulated from the patient. That is, exposed surfaces of the jaws 501-502 may be coated with a nonconductive layer to insulate the outer surfaces of the jaws 501/502 from tissue.

In a bipolar embodiment, upper jaw 501 and lower jaw 502 are isolated from each other, and bipolar energy can be delivered between the two jaws. During surgery, jaw 502 and the contact surface 517 of the bent cam 504 of the jaw 501 may be selectively energized with energy from an electrosurgical generator over a wire, such as wire 113b shown in FIG. 3 that extends through the shaft to a connector at the opposite end of the tool.

Otomy feature 506 and contact base 507 are electrically isolated from the lower jaw 502. The contact surface 517 is selectively used to energize the otomy feature 506 in a safe manner, in response to a predetermined range of open angles between the jaws (e.g., 60-65 degrees). Accordingly, an exposed tip 516 of the otomy feature 506 extending from the jaw 502 can be selectively energized in response and used to cauterize, cut, or ablate tissue. Below the predetermined/specified jaw angle (JA) the otomy feature 506 is electrically floating. Once the upper jaw 501 is opened past a certain specified angle (JA), contact surface 517 touch contact base 507. If bipolar energy is delivered when the jaws are at or past the specified jaw angle (JA), bipolar energy will be flowing between the lower jaw and the otomy feature/tip 506/516 (as well as the upper jaw).

Alternatively, monopolar energy could be delivered to the upper jaw 501, which would energize the otomy feature/tip with monopolar energy when the jaws are opened to the specified angle (JA). A ground electrode 114 shown in FIG. 1A is coupled to the patient body, if monopolar energy is being utilized for electrosurgical procedures.

The upper jaw 501 is rotatably coupled to the lower jaw 502 at coupling pin 505. Alternatively, coupling pin 505 may be substituted for other types of mechanical fasteners such as a rivet, or a bolt and nut that pivotally couples jaw 501 to jaw 502. In this exemplary embodiment, jaw 502 is fixed to wrist 503 and does not rotate with respect to the coupling pin 505. End effector 500 is actuated by rotating the jaw 501 open and close about a pivot axis at the coupling pin 505.

FIG. 5A illustrates a side view of the electrosurgical end effector 500 with the otomy feature 506 exposed in a cut out view for purpose of illustration. The otomy feature 506 is a fixed rod with an otomy tip 516 that slightly protrudes from the lower jaw 502. That is, the otomy feature 506 is fixed in a rigid position within the lower portion of jaw 502. Most of the otomy feature 506 is surrounded in a nonconductive shroud or sheath 508 that is a part of the structure of the bottom jaw 502. However, the tip or end 516 of the otomy feature 506 is exposed and protrudes slightly from the nonconductive sheath 508. Shroud 508 electrically isolates otomy feature 506 from lower jaw 502. Otomy feature 506 is electrically floating until the jaws are opened past a specified jaw angle (JA).

At the other end of the otomy feature 506, opposite the protruding otomy tip 516, the otomy feature 506 includes a contact base 507 that is coupled to the fixed rod of the otomy feature 506. The otomy feature 506, including the otomy tip 516, fixed rod, and contact base 507 are all conductive, typically being formed of steel, and electrically coupled together.

The contact surface 517 that is part of the bent cam portion 504 of the jaw 501, is configured to couple to the contact base 507 when the jaw 501 is pivotally opened. As the jaw 501 opens, the bent cam portion 504 of the jaw 501 rotates clockwise towards the contact base 507. With further rotation, the contact surface 517 of the bent cam portion 504 eventually makes contact with the contact base 507 of the otomy feature. In this manner, when coupled together, the otomy feature 506 can be selectively energized by an electrosurgical generator over a wire, such as the wire 113b shown in FIG. 3.

The jaws 501 and 502 of the electrosurgical end effector 500 can be opened and closed over a predetermined range of angles (e.g., 0 to 65 degrees). During normal use as a surgical grasper, jaws 501 and 502 may be opened up to but below a predetermined energizing jaw angle JA (e.g., 60 degrees) between each jaw without energizing the otomy tip 516. Below the predetermined energizing jaw angle, the contact base 507 and the otomy feature 506 remain isolated from the electrosurgical generator. Accordingly, the exposed otomy 516 tip is not energized below the predetermined energizing jaw angle JA so that tissue that may come in contact with otomy tip 516 and not be cauterized or burnt.

Figure 5B:
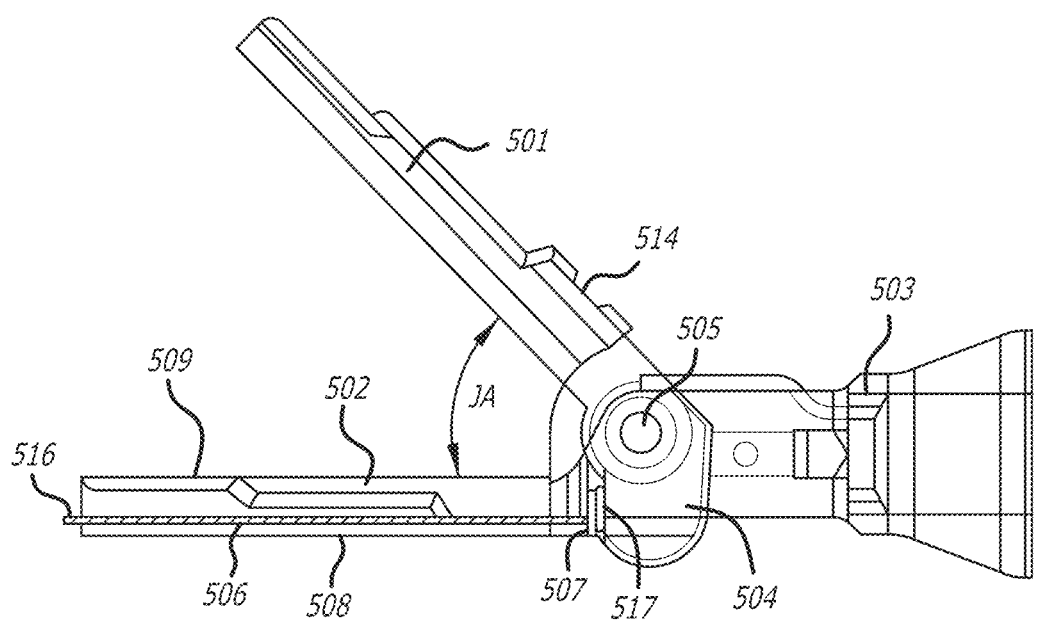

FIG. 5B illustrates the jawed end effector 500 of FIG. 5A in an open position with the otomy feature 506 ready for electrosurgery use. When the jaw 501 is opened past the predetermined jaw angle JA (e.g., 60 degrees), the contact base 507 and contact surface electrode 517 are coupled together as shown in FIG. 5B, so that the otomy feature 506 is selectively energized by an electrosurgical generator. The jaw 501 may continue to be opened further for one or more degrees more (e.g., 1-5 degrees) past the jaw angle JA so that the contact base 507 and contact surface electrode 517 are more substantially coupled together. The predetermined jaw angle is a function of the angle between the working portion 510 and the angled or bent cam portion 504 of the pivotal jaw 501.

When an electrosurgical generator is coupled to the tool and energized, the wire 113a couples electrical energy into the contact surface 517. With the jaw 501 sufficiently open at or past the jaw angle JA, the electrical energy is coupled to the contact base 507 and to the otomy tip 516 of the otomy feature 506. In this case, when touching the exposed otomy tip 516 to tissue, that electrical energy can be transferred into the touched tissue making contact with the exposed otomy tip. To decouple the electrical energy from the exposed otomy tip, the pivotal jaw 501 is closed thereby reducing the open jaw angle between jaws 501-502 below the predetermined jaw angle JA.

Figure 6A:
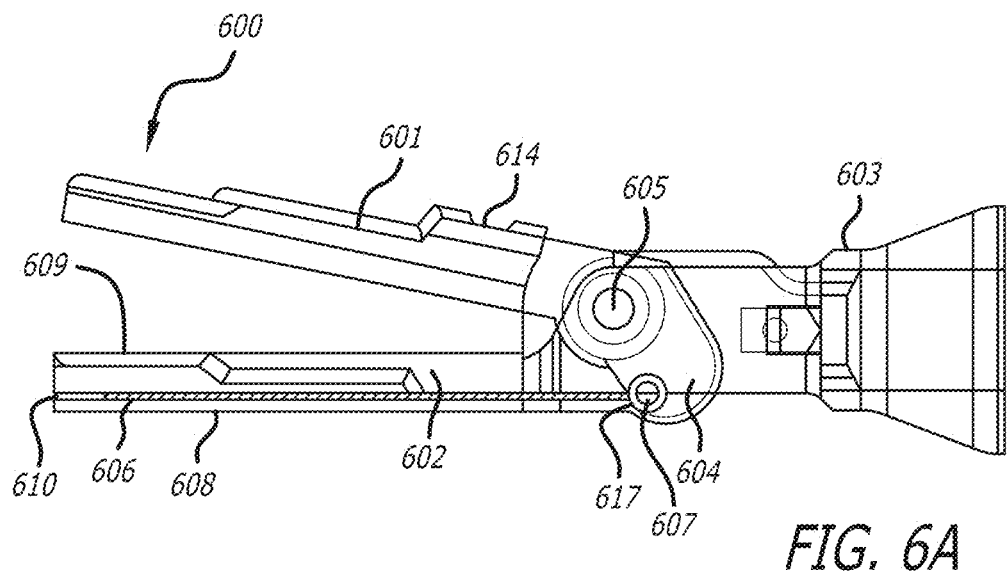
FIGS. 6A-6B illustrate another exemplary end effector of a surgical tool with otomy feature used in a teleoperational assembly such as one shown in FIG. 1B.
Figure 6B:
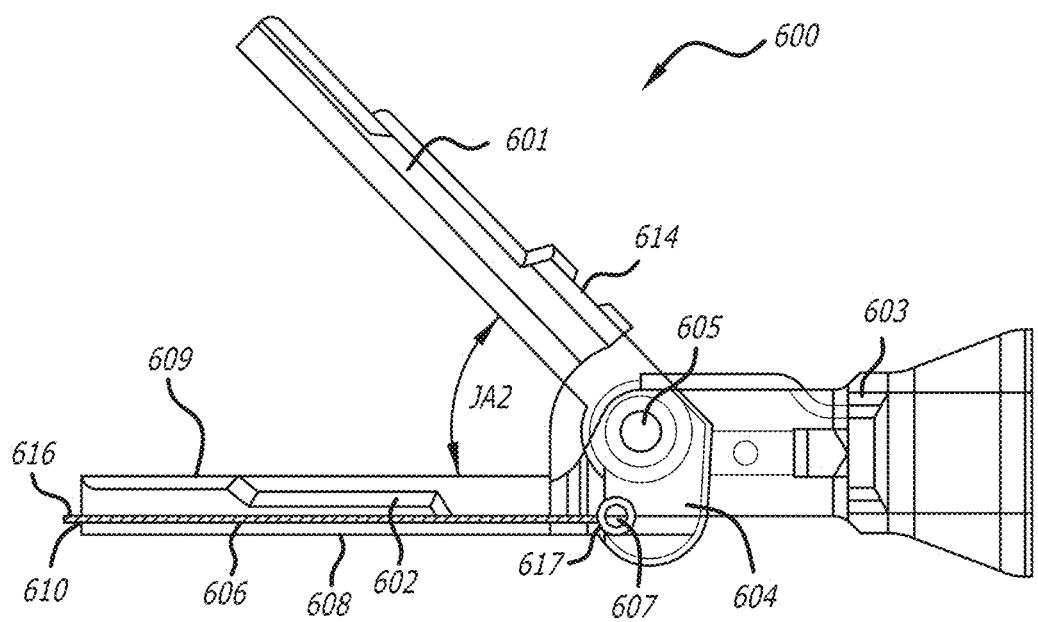

Referring now to FIGS. 6A-6B, an electrosurgical end effector 600 is coupled to a wrist component 603 (see description of wrist 203 shown in FIG. 2A) of a tool. The electrosurgical end effector 600 includes a pivotal jaw 601 and a fixed jaw 602. Jaw 601 is pivotally coupled to the fixed jaw 602 at a coupling pin 605.

The pivotal jaw 601 includes a working portion 614 at an angle with a lever/cam portion 604. The lever/cam portion 604 is separated from the working portion 614 by a pivotal pin opening defining a dividing line between each. The coupling pin 605 is inserted within the pivotal pin opening.

Electrosurgical end effector 600 is shown as a tissue grasper or a tissue sealer, however other types of end effectors and surgical tools may also benefit from the inventive concepts disclosed herein. Inner jaw surface 609 may be conductive, and when energized, would act as a sealing/cauterizing electrode. Alternatively, inner jaw surface 609 may include one or more electrodes for sealing, desiccating, or cauterizing vessels and tissue.

The fixed jaw 602 further includes an otomy feature 606 that can be constantly energized by an electrosurgical generator. As a safety feature, the otomy feature 606 is slideable. An otomy tip 616 at one end of the rod of the otomy feature 606 slides in and out through an opening 610 in the jaw and nonconductive shroud 608 wrapped around the jaw. Shroud 608 is an insulator and electrically isolates otomy feature 606 from the lower jaw 602. At an opposite end of the rod, the otomy feature includes a rod opening 617 coupled to the rod. The rod opening 617 is pivotally coupled like a connecting rod to a pin 607 of the cam portion 604 of the jaw 601. Accordingly, the pivoting motion of the cam portion 604 is translated into a linear reciprocating motion of the rod of the otomy feature 606.

Ordinarily the otomy feature 606 is hidden within a tunnel of the shroud 608 of the fixed jaw 602. When otomy is desired, the pivotal jaw 601 is opened to a jaw angle JA sufficient to protrude the tip 616 of otomy feature 606 from the shroud 608, such as shown in FIG. 6B. Comparing FIGS. 6A-6B, as the jaw 601 opens, its cam portion 604 rotates clockwise. With the rod opening 617 of the otomy feature pivotally coupled to the pin 607, clockwise rotation of the cam portion 604 slides the otomy feature 606 outward from the shroud 608 towards the opening 610. Further opening of the pivotal jaw 601 results in additional clockwise rotation of the cam portion 604 to slide the otomy tip 616 out from the opening 610. In FIG. 6B, the jaw 601 is opened to a jaw angle JA2 with the fixed jaw 602 such that the otomy tip 616 is substantially extended out of the opening 610 away from the end of the jaw.

The otomy tip 616 extends out over a range of jaw angles. The otomy tip is even with the end of the jaw at a first jaw angle JA1 (not shown). The otomy tip is substantially extended out from the jaw at a second jaw angle JA2. These first and second jaw angles are a function of the length of rod of the otomy feature, length of the jaw/tunnel, and the cam angle (bend of cam portion) between an axis of the cam portion through the pivot pin and an axis of the pivotal jaw through the pivot pin. With cam angle fixed, a longer rod for the otomy feature 606 will have the otomy tip protruding out from opening 610 at a more acute (smaller) jaw angle. With a fixed rod length, a greater cam angle (sharper bend) between the working portion 614 and the cam portion 604 of the jaw, the otomy feature 606 will start the otomy tip protruding out from opening 610 at a more acute jaw angle.

An exemplary second jaw angle JA2 is 50 degrees but it should be understood that other jaw angles may be used to substantially extends the tip of the otomy feature 606 from opening 610.

Figure 7A:
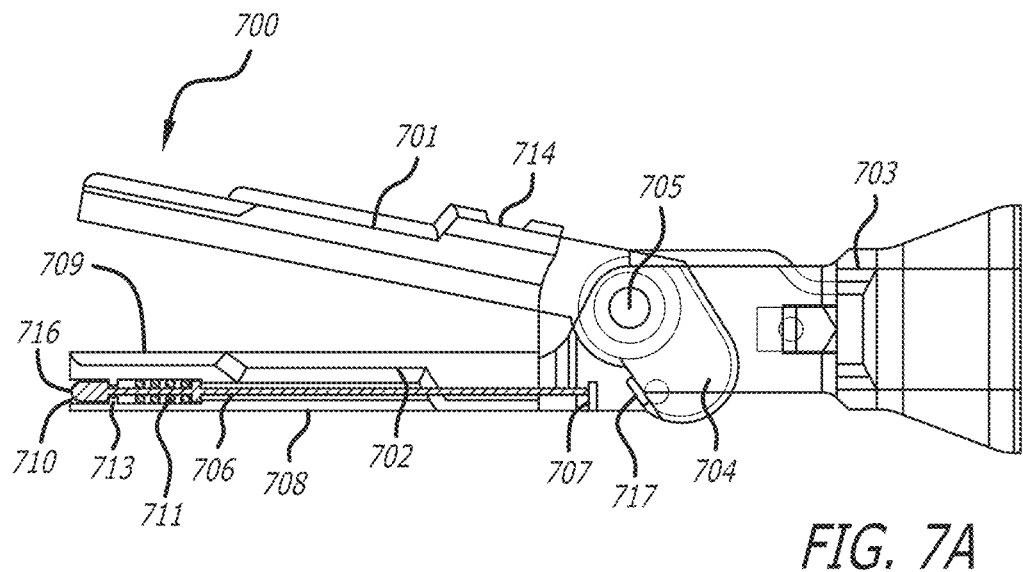
FIGS. 7A-7B illustrate another exemplary end effector of a surgical tool with otomy feature used in a teleoperational assembly such as one shown in FIG. 1B.
Figure 7B:
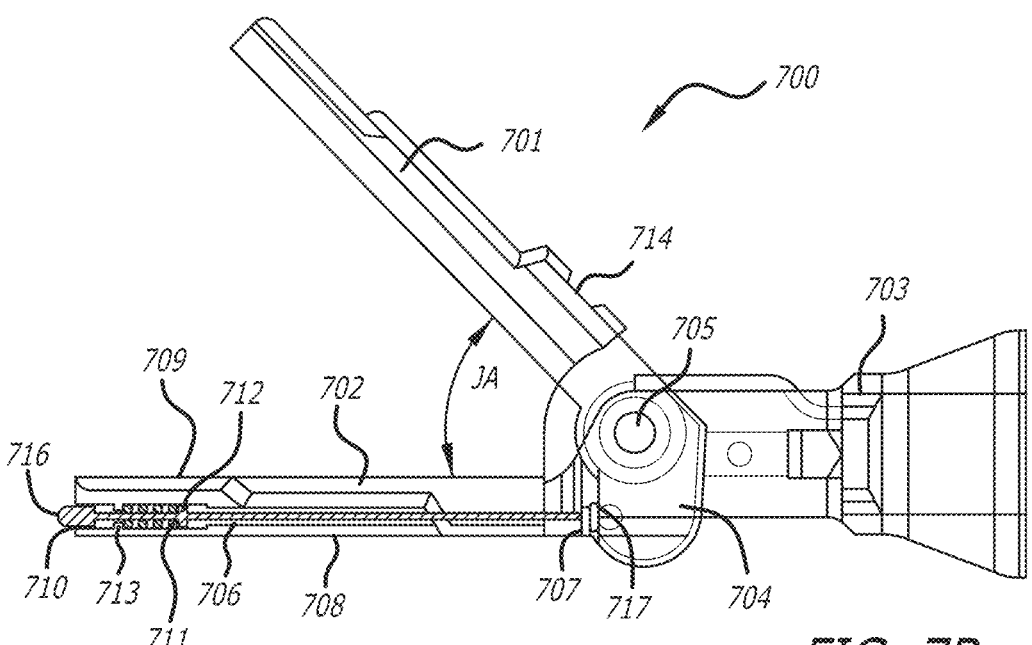

Referring now to FIGS. 7A-7B, an electrosurgical end effector 700 for an electrosurgical tool is shown coupled to a wrist 703 (similar to wrist 203 of FIG. 2E). The end effector 700 is illustrated in a side view with parts being rendered transparent to show the inner workings of some components. The end effector 700 includes a pivotal jaw 701 rotatably coupled to a fixed jaw 702 at a coupling pin 705.

The pivotal jaw 701 includes a working portion 714 and a lever/cam portion 704 with a pin opening defining a dividing line between each. The coupling pin 705 is inserted into the pin opening to pivotally couple the pivotal jaw 701 to the fixed jaw 702. With axes along each through the coupling pin 705, the lever/cam portion 704 is bent at an angle with respect to the working portion 714.

End effector 700 is shown as a tissue grasper. However it should be understood that the embodiments of the invention are not limited to only a tissue grasper type of end effector. Other surgical instruments, such as a tissue sealer, may also benefit from the inventive concepts disclosed herein. In a tissue sealer embodiment of the invention, inner jaw surface 709 may be conductive, and when energized, would act as a sealing electrode. Alternatively, inner jaw surface 709 may include one or more electrodes for sealing, desiccating, or cauterizing vessels and tissue.

In a lower portion, the fixed jaw 702 further includes an otomy feature 706 within a tunnel formed by a shroud 708. The otomy feature 706 comprises a rod with an otomy tip 716 at one end and an otomy base 707 at an opposite end. Between the otomy tip 716 and the otomy base 707, the otomy feature 706 further includes a flange or collar 712. The diameter of the otomy tip 716 may be greater than diameter of the rod shaped body of the otomy feature 706 to cauterize a larger area of tissue. The otomy feature 706 is formed of a conductive material to transfer energy between ends.

The shroud 708 surrounding the otomy feature 706 forms the hollow tunnel with an opening 710 at the distal end of jaw 702. The otomy tip extends and retracts through the opening 710 out of the tunnel. The shroud 708 around the rod of the otomy feature 706 is made of a nonconductive or insulative material. Shroud 708 is an insulator and electrically isolates the otomy feature 706 from the lower jaw 702. To provide a measure of safety, the otomy feature 706 electrically floats until the jaws are opened past a predetermined jaw angle (JA) where a surface 717 of the cam portion 704 of the jaw and an otomy base 707 of the otomy feature 706 connect together.

The otomy feature 706 is spring loaded and slides along the tunnel to expose and hide the otomy tip 716 in the tunnel. A spring 711 is coiled over the rod of the otomy feature 706. One end of the spring 711 abuts the collar 712 and an opposite end abuts a stop ring 713 in the tunnel. A portion of the rod extends through a center opening in the stop ring 713 to the tip 716.

The force of the spring 711 biases the otomy feature 706 into a retracted position relative to opening 710. In this case, the force of the spring 711 pushes on the collar 712 to slide the tip of the otomy feature back into the tunnel. The distal stop ring 713 also retains the spring 711 within the tunnel and keeps it from being dislodged out from the opening 710. The stop ring 713 also advantageously blocks the otomy tip 716 from extending too far out from the tunnel.

Referring now to FIG. 7B, the jaw 701 is pivoted around the pin 705 over a range of angles between the jaws 701-702. When otomy is desired, the pivotal jaw 701 is opened past a predetermined jaw angle JA with the fixed jaw 702. A surface 717 of the cam portion 704 of the jaw rotates clockwise and pushes out on the otomy base 707. The force applied against the otomy base 707 overcomes the spring tension of the spring 711 to force the otomy tip 716 to protrude from the opening 710 into an extended position past end of jaw 702. When the jaw 701 closes below the predetermined jaw angle JA, the spring 711 pushes against the collar 712, returning the otomy tip 716 of the otomy feature 706 back to its retracted position within the tunnel.

The contact surface 717 of the cam portion 704 may be conductive to couple to the otomy base 707, and supply energy to the otomy feature 706 and its tip 716, when the jaws are open to a specified angle, and a connection is made between the two components. Alternatively, a wire (e.g., wire 113b in FIG. 3) may be directly coupled to the rod or base of the otomy feature to supply energy to the tip.

Figure 8A:
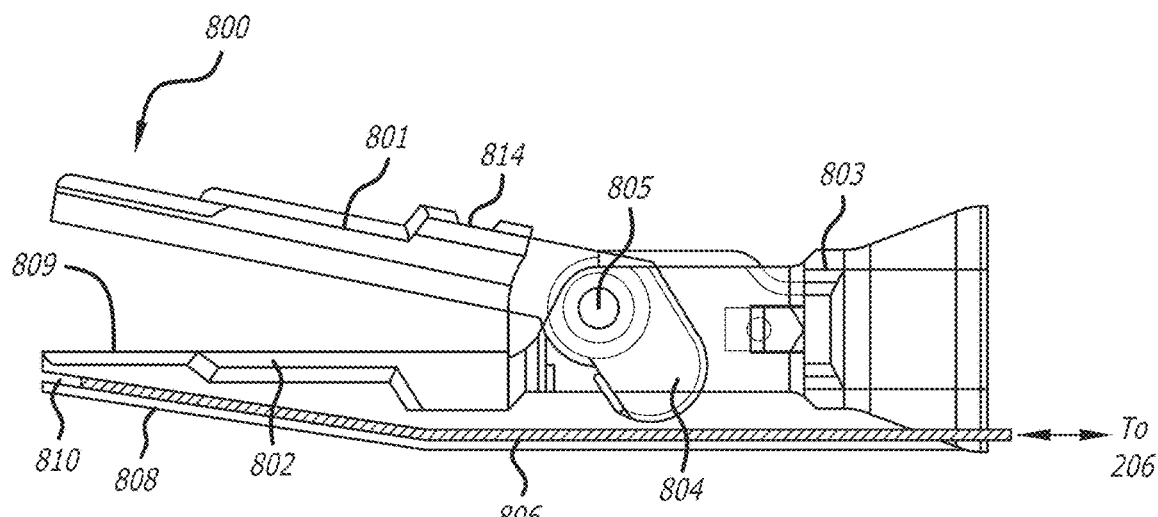
FIGS. 8A-8B illustrate yet another exemplary end effector of a surgical tool with otomy feature used in a teleoperational assembly such as one shown in FIG. 1B.
Figure 8B:
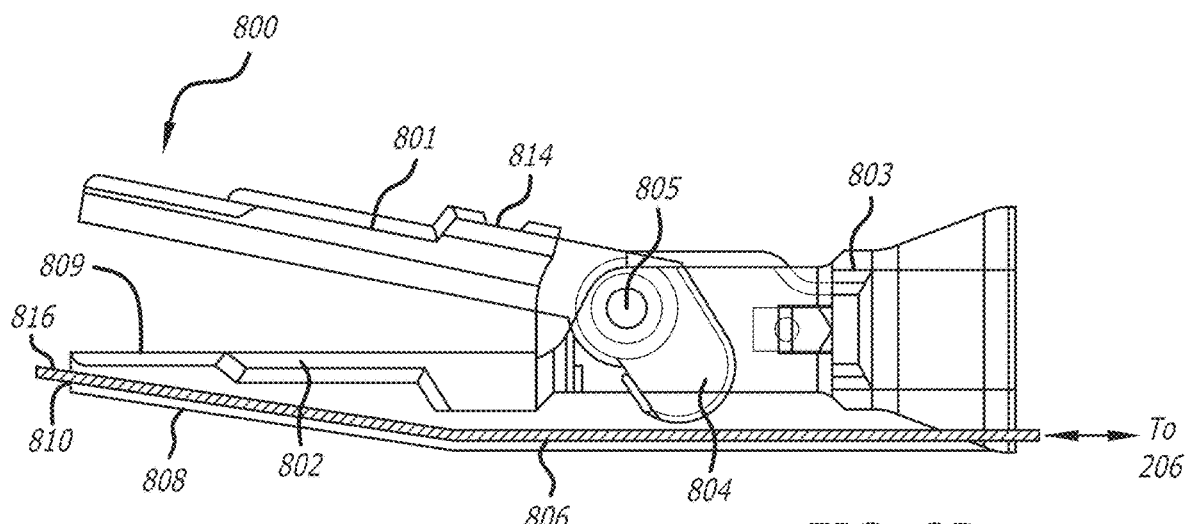

Referring now to FIGS. 8A-8B, an electrosurgical end effector 800 is shown coupled to a wrist 803 of an electrosurgical tool. The electrosurgical end effector 800 also may be referred to as a jawed end effector or simply end effector. The end effector 800 includes a pivotal jaw 801 and a fixed jaw 802 coupled together at coupling pin 805. The pivotal jaw 801 pivots about the coupling pin 805. Pivotal jaw 801 includes a bent cam portion 804 and a working portion 814. The fixed jaw 802 is coupled to the wrist 803 and does not rotate or pivot about the coupling pin 805.

The end effector shown in FIG. 8A-8B is a tissue grasper. However it should be understood that the embodiments are not limited to only a tissue grasper end effector. Other surgical instruments, such as a tissue sealer, may also benefit from the inventive concepts disclosed herein. In the case of a tissue sealer embodiment, the fixed jaw 802 may have a conductive inner jaw surface 809, that when energized, may be used to seal, desiccate, or cauterize tissue and vessels between the jaws 801 and 802. Alternatively, one or more electrodes may be placed on the inner jaw surface 809 to serve the same function.

Near a bottom portion, the fixed jaw 802 further includes an otomy feature 806 that slides inside a tunnel. The otomy feature 806 is surrounded by a shroud 808 that forms the tunnel. Shroud 808 is an insulator and electrically isolates the otomy feature 806 from the jaw 802. When otomy is desired, the tip 816 of the otomy feature 806 is extended past the distal end of jaw 802. Actuation of the otomy feature 806 shown in FIGS. 8A-8B is not a function of a jaw angle or rotation of the pivotal jaw 801 about the pin 805. The otomy feature 806 is driven by transmission and/or driver in an interface base (e.g., interface base 208 shown in FIG. 4) with mechanical and electro-mechanical components independent of jaw angle or rotation of the pivotal jaw 801 with the fixed jaw 802.

The otomy feature 806 shown in FIGS. 8A-8B is not a function of a jaw angle or rotation of the pivotal jaw 801. Instead, the otomy feature 806 is controlled independent of the pivotal jaw 801. The otomy feature 806 may be controlled by one of the inputs/drivers or an electric motor of the interface base.

For example, the rod of the otomy feature 806 is coupled to a shaft, such as shaft 206 shown in FIG. 3. The shaft 206 may be controlled by an electric internal driver motor 256. Alternatively, the shaft 206 may be controlled by an input shaft 254 coupled to an input receiver driven by a rotatable driver.

In the case of the driver motor 256, an electrical signal is used to control the driver motor to pull in and pay out the shaft 206. As shown in FIG. 4, a rack and pinion driver transmission 258 is coupled between the driver motor 256 and the shaft 206. The driver motor 256 is controlled by electrical signals received from a master control console, such that the otomy feature 806, is driven separately from the grip drive mechanism that opens and closes the pivotal jaw 801. In this way the actuation of the otomy feature may be controlled independent of the jaw angle between the jaws 801-802. The otomy feature 806 may be driven from the lower jaw 802 at any jaw angle.

Similarly, the electrosurgical energization of the otomy feature 806 is controlled independent of the jaw angle between the jaws 801-802. Control signals can be sent from the surgeon console 120 to a monopolar generator 110A or a bipolar generator 110B to couple electrical energy into the otomy tip 816 regardless of jaw angle.

Alternatively, the otomy feature 806 may responsive to the pivotal jaw 801 and the jaw angle between jaws 801-802. For example, with pivotal jaw 801 open to a first jaw angle (JA1), energy may be supplied to the otomy feature 806 and its otomy tip. Further opening the pivotal jaw 801 to a second jaw angle (JA2) greater than the first jaw angle, the shaft of the otomy feature may be slid along the tunnel such that the otomy tip is extended from the end of the jaw 802. Accordingly, the pivotal jaw 801 can be opened and closed in order to control the otomy feature 806.

Of course, those having ordinary skill in the art after reading this disclosure will appreciate that a variety of actuation mechanisms, including but not limited to, for example, servo actuators associated with a teleoperated robotic surgical system or a manually driven actuator can be utilized to control the movement of the otomy feature 806.

Otomy Accessory Tool

During surgery, different tissue effects are needed at different times of the procedure. During surgery it may be desired to use a surgical instrument to create holes in certain target anatomy (i.e., stomach, bowel, or mesentery) to accomplish a surgical task. Typically to obtain a tissue effect such as an otomy, a defect must be created in the tissue. Electric fields for otomy creation are generated with different shapes than are desired for manual tissue manipulation. This may be achieved using monopolar energy instruments (such as a hook, spatula, or monopolar curved scissors), an advanced energy instrument incorporating a monopolar tip (such as LIGASURE ADVANCE laparoscopic instrument by MEDTRONIC PLC), or an ultrasonic shear (such as HARMONIC ACE+7 shears by ETHICON US, LLC) with electrosurgical vessel sealing.

Referring now to FIGS. 9A-9D, an otomy accessory tool 910 is shown for coupling to a bipolar electrosurgical end effector 900 of an electrosurgical tool. FIGS. 10A-10D, illustrate an otomy accessory tool 1010 for coupling to the bipolar electrosurgical end effector 900. The otomy tip 915 of the otomy accessory tool 910 differs from the otomy tip 1015 of the otomy accessory tool 1010.

For the embodiments shown in FIG. 9A and FIG. 10A, an upper jaw 901U includes at least a first electrode (e.g., a conductor) 902 disposed on or near an interior surface of the upper jaw. The lower jaw 901L includes at least one second electrode 903 disposed on or near an interior surface of the lower jaw. The first electrode 902 and the second electrode 903 can be energized by a bipolar electrosurgical generator. Alternatively, with the patient and patient tissue coupled to ground, the second electrode 903 may be energized by a monopolar electrosurgical generator. In yet another embodiment, an advanced electrosurgical generator that generates multiple voltages can be used to energize the first electrode 902 and the second electrode 903 with respect to a third electrode (not shown).

Bipolar radio frequency (RF) energy can be used with the otomy accessory tool 910,1010 to form an otomy in tissue, with less charring of tissue and less smoke—that can obscure a surgeon's view. Using Bipolar RF energy also avoids the complications associated with using monopolar energy, such as capacitive coupling. The otomy accessory tool 910,1010 being an accessory to an electrosurgical device can be optimized for otomy creation. A variety of otomy accessory tools may be provided with different sized tool tips 915,1015 to provide different sized otomies in tissue. The end effector 900 can have a differing geometry that is better optimized for performing other more common minimally invasive surgical procedures.

FIG. 9A shows the first electrode 902 of a jaw coupled to the first tool section 912 and the second electrode 903 of a jaw coupled to the second tool section 913 of the otomy tool 910. The first tool section 912 and second tool section 913 are conductive conductors of electricity separated by a non-conductive insulator 914. The second tool section 913 includes a tool tip 915 that when energized can produce an otomy in tissue that it contacts.

For some embodiments, the first tool section 912 is coupled to a first power supply terminal of an electrosurgical generator and the second tool section 913 and tool tip 915 is coupled to a second power supply terminal of the electrosurgical generator. When the tool tip 915 and the first tool section 912 concurrently contact contiguous tissue a circuit is completed with the electrosurgical generator and an otomy can be formed in tissue. In some surgical applications, tool tip 915 will contact tissue prior to first tool section 912 and the otomy formation begins when first tool section 912 contacts the tissue thereby forming a complete circuit and enabling otomy formation. For the embodiment shown in 9A, the tool tip 915 extends outwards beyond insulator 914 but not upwards beyond insulator 914 towards the first tool section.

FIG. 10A shows the first electrode 902 of a jaw coupled to the first tool section 1012 of the otomy tool 1010 and the second electrode 1003 of a jaw coupled to the second tool section 1013 of the otomy tool 1010. The second tool section 1013 includes the tool tip 1015. The first tool section 1012 and the second tool section 1013 (including the tool tip) are conductive conductors of electricity separated by a non-conductive insulator 1014.

For some embodiments, the first tool section 1012 is coupled to a first power supply terminal of an electrosurgical generator and the second tool section 1013 and tool tip 1015 is coupled to a second power supply terminal of the electrosurgical generator.

The otomy tip 1015 of the otomy accessory tool 1010 differs from the otomy tip 915 of the otomy accessory tool 910. The otomy tip 1015 extends outwards beyond insulator 1014 and upwards to approximately the same height of the top of the first tool section 1012 at its most forward extent. The otomy tip 1015 is configured to perform a larger otomy formation in tissue when energized.

When the tool tip 1015 and the first tool section 1012 are energized and concurrently or simultaneously contact contiguous tissue, a circuit is completed with the electrosurgical generator and an otomy can be formed in tissue. In some surgical applications, tool tip 1015 will contact tissue prior to first tool section 1012 and the otomy formation begins when first tool section 1012 contacts the tissue thereby forming a complete circuit and enabling otomy formation.

Otomy formation in tissue is less frequently performed than other functions of a surgical tool. The otomy accessory tool provides otomy formation. Accordingly, the end effector 900 and the surgical instrument of which it is a part can be designed and optimized for other tasks performed with greater frequency (such as grasping or blunt dissection).

To use the otomy accessory tool, the surgeon controls an instrument to grasp a graspable portion of the otomy accessory tool between the jaws of the instrument. The otomy accessory tool is configured such that when grabbed, one electrically conductive portion of the otomy accessory tool contacts one electrode surface, and an opposing electrode surface contacts a second electrically conductive portion of the otomy accessory tool. The second electrically conductive portion is insulated from the first electrically conductive portion of the otomy accessory tool. The first conductive portion of the otomy accessory tool is configured to provide a robust electrical path (e.g., large cross-sectional area presented to tissue). The second electrically conductive portion of the otomy accessory tool includes an otomy tip 915,1015. The otomy tip 915,1015 can be shaped in a manner optimal for performing bipolar cutting (e.g., a minimal cross-sectional area situated proud of the return surface provided by the first tool section 912,1012).

Rather than including a permanently affixed geometry in an instrument for the creation of otomies, the otomy accessory tool 910,1010 allows a surgeon to selectively use one of a plurality of otomy accessory tools with different geometries whenever it is desired to create an otomy.

The otomy accessory tool 910,1010 creates electrical pathways to its tip through the sealing/grasping electrodes of the electrosurgical device. The electrosurgical generator can apply a different mode of energy (e.g., cutting energy instead of sealing energy) to get the desired cutting effect to occur at the tip of the otomy accessory tool.

The otomy accessory tool 910,1010 is placed between the tips of the jaws 901U, 901L of the instrument prior to insertion into a patient. After insertion into the patient, one or more otomies in tissue can be formed with the otomy accessory tool 910,1010. After creation of the one or more otomies, the otomy accessory tool 910,1010 can be removed from the patient. Alternatively, the otomy accessory tool 910,1010 can be retained in the surgical cavity over a surgical site. If the instrument needs to be free to perform other functions, the otomy accessory tool can be placed into and grasped by the jaws of another grasping instrument for later use.

FIG. 9B illustrates a bottom view of end effector 900 grasping the otomy accessory tool 910. The otomy tip 915 is integral with the second tool section 913 of the otomy accessory tool. The electric potential of second tool section 913 and otomy tip 915 is set by the second electrode 903 of the lower jaw 901L.

FIG. 10B illustrates a bottom view of end effector 900 grasping the otomy accessory tool 1010. For some embodiments, the tool tip 1015 is integral with second tool section 1013. The electric potential of second tool section 1013 is set by second electrode 903, which is a component of lower jaw 901L.

FIGS. 9C and 10C illustrate respective cross-sectional views of corresponding accessory tools 910 and 1010. Insulator 914,1014 provides electric separation of first tool section 912,1012 from second tool section 913,1013. For some embodiments, the first tool section 912,1012 provides a return path for current from the otomy tissue to a ground terminal or a first terminal of an electrosurgical generator. The otomy tip 915 of the accessory tool 910 extends upwards no farther than a plane of the insulator 914. The otomy tip 1015 of the accessory tool 1010 extends upwards substantially past a plane of the insulator 1014. Generally, the otomy tip 1015 can form a larger otomy in tissue than otomy tip 915.

Figure 9D:
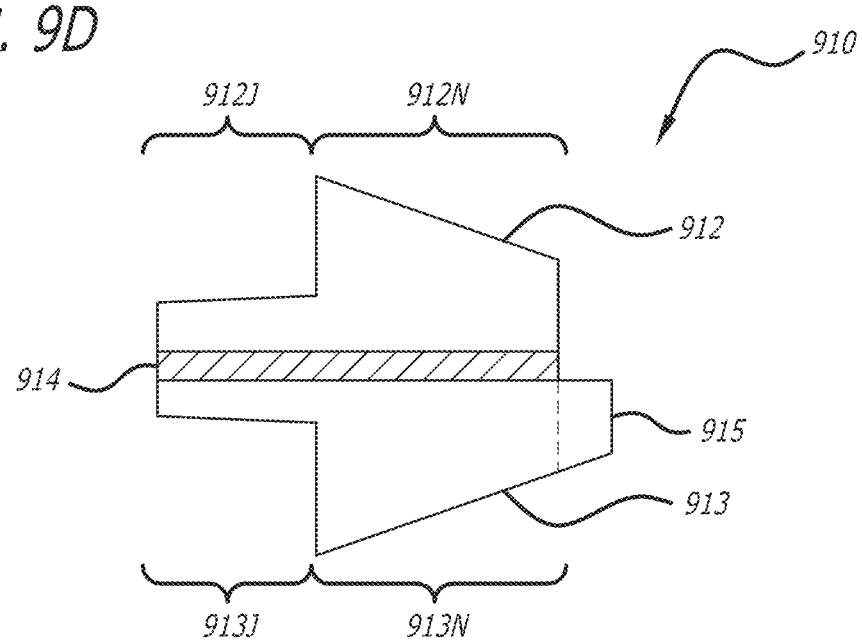
Figure 10D:
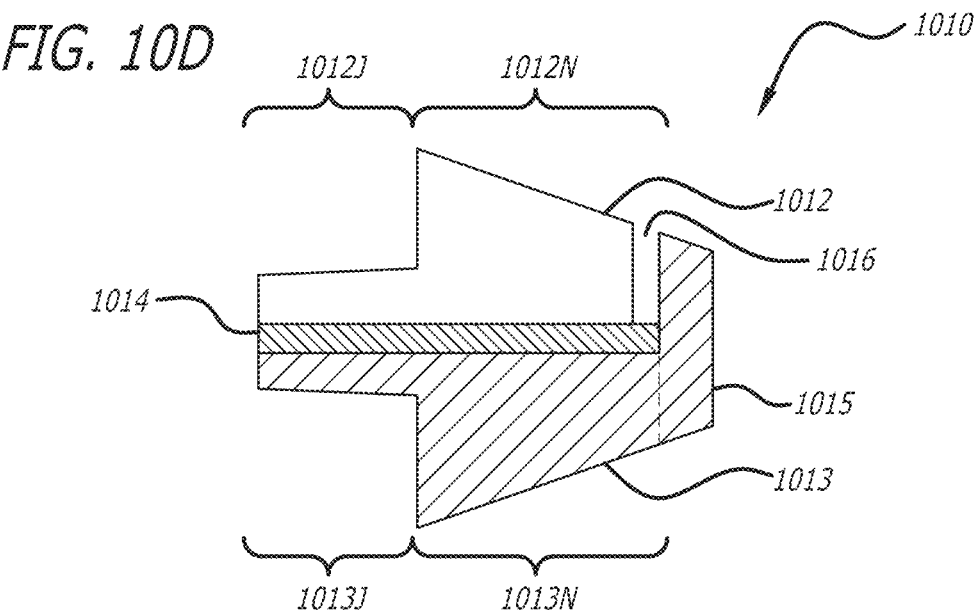

FIGS. 9D and 10D respectively illustrate a side view of the corresponding otomy accessory tool 910,1010. The first tool section 912,1012 includes a first junction portion 912J, 1012J and a first nose portion 912N,1012N. The second tool section 913,1013 includes a second junction portion 913J, 1013J and a second nose portion 913N,1013N. The first junction portion 912J,1012J and the second junction portion 913J,1013J of the otomy accessory tool are thin in order to be clamped between the upper jaw 901U and the lower jaw 901L of the electrosurgical end effector 900 of an electrosurgical tool. As shown in the cross section view of FIGS. 9C and 10C, the first nose portion 912N,1012N and the second nose portion 913N,1013N expand in size from the junction portions and then narrow down in size to work effectively with the otomy tip 915,1015. The insulator 914 for this embodiment is a plane of insulating material between inner surfaces of the first tool section 912,1012 and the second tool section 913,1013.

The first junction portion 912J,1012J of the first tool section 912,1012 is configured to be received by the upper jaw 901U of the electrosurgical end effector 900. The first junction portion 912J, 1012J makes electrical contact with the first electrode 902 in the upper jaw 901U.

The second junction portion 913J,1013J of the second tool section 913,1013 is configured to be received by the lower jaw 901L of the electrosurgical end effector 900. The second junction portion 913J, 1013J makes electrical contact with the second electrode 903 in the lower jaw 901L.

The tool tip 1015 in one embodiment is shown to extend upwards substantially further than insulator 1014. The portion of the tip 1015 extending up above the plane of the insulator 1014 is separated from the first nose portion 1012N by a gap 1016.

The otomy accessory tool 910,1010 can be used with various remotely controlled electrosurgical instruments coupled to various electrosurgical generators. With a typical bipolar electrosurgical instrument (e.g., a vessel sealer), the first electrically conductive portion of the otomy accessory tool contacts the conductive sealing surface of one jaw of the instrument, while the second electrically conductive portion of the otomy accessory tool contacts the conductive sealing surface of the opposing jaw. The two electrically conductive portions of the otomy accessory tool are electrically insulated from the other by an insulator. To perform an otomy, bipolar cut energy from a bipolar electrosurgical generator energizes the typical bipolar electrosurgical instrument such that the bipolar cut energy is coupled into the associated features of the otomy accessory tool.

An electrosurgical instrument with two electrodes (e.g., a seal electrode and a return electrode) can also be used with the otomy accessory tool 910,1010. Similar to a bipolar instrument, when the electrosurgical instrument grasps the otomy accessory tool, contact is made between the first conductive portion of the otomy accessory tool and the return electrode in one jaw. The second conductive portion of the otomy accessory tool makes contact with the seal electrode in the other jaw. The energy present on the two electrodes of the electro surgical instrument is sufficient to create an otomy.

The otomy accessory tool 910,1010 can be used with mono-polar energy generated by a mono-polar electrosurgical generator. The monopolar energy from the mono-polar electrosurgical generator can be applied to one or both jaws of a bipolar electrosurgical instrument. While the tissue of a patient is grounded, the monopolar energy is coupled into the second electrically conductive portion of the otomy accessory tool and the otomy tip. The monopolar energy can also be coupled into the first electrically conductive portion of the otomy accessory tool. Because the conductive portions of the otomy accessory tool are electrically isolated from each other, there is little risk of damage to the bipolar electrosurgical instrument and the otomy accessory tool.

CONCLUSION

Each end effector 500,600,700,800 shown in the figures and described above may be an instance of the end effector 202 of the tool 201 shown in FIG. 2A. Although certain exemplary embodiments and methods have been described in some detail, for clarity of understanding and by way of example, it will be apparent from the foregoing disclosure to those skilled in the art that variations, modifications, changes, and adaptations of such embodiments and methods may be made without departing from the true spirit and scope of the invention. This disclosure contemplates other embodiments or purposes.

For example, it will be appreciated that one of ordinary skill in the art will be able to employ a number of corresponding alternative and equivalent structural details, such as equivalent ways of fastening, mounting, coupling, or engaging tool components, equivalent mechanisms for producing particular actuation motions, and equivalent mechanisms for delivering electrical energy. As another example, structural details from one embodiment may be combined with or utilized in other disclosed embodiments. Therefore, the above description should not be taken as limiting the scope of the invention which is defined by the appended claims.

What is claimed is:

1. An electrosurgical end effector comprising:
a first end effector jaw;
a second end effector jaw coupled to the first end effector jaw;
a coupling pin extending through the first end effector jaw and the second end effector jaw, the coupling pin configured to rotatingly couple the first end effector jaw to the second end effector jaw;
an actuation mechanism coupled to an end of the first end effector jaw to rotate the first end effector jaw about the coupling pin;
an otomy feature coupled to the second end effector jaw; and
a first electrical conductor to electrically couple the otomy feature to a generator;
wherein the otomy feature is electrically activated by contact with a cam portion of the first end effector jaw;
wherein the cam portion of the first end effector jaw rotates in a first direction about the coupling pin, and at a predetermined jaw angle, the cam portion contacts a base of the otomy feature conducting electrical energy to the otomy feature.

2. The electrosurgical end effector of claim 1, wherein the otomy feature is electrically active when the first end effector jaw is opened at and beyond the predetermined jaw angle about the coupling pin with respect to the second end effector jaw; and the otomy feature is electrically inactive when the first end effector jaw is opened below the predetermined jaw angle about the coupling pin with respect to the second end effector jaw.

3. The electrosurgical end effector of claim 1, wherein the first end effector jaw is electrically isolated from the second end effector jaw.

4. The electrosurgical end effector of claim 1, wherein the otomy feature is actuated by the actuation mechanism that rotates the first and second end effector jaws.

5. The electrosurgical end effector of claim 1, wherein the otomy feature is slideably housed in the second end effector jaw and opening the first end effector jaw past the predetermined jaw angle causes the cam portion of the first end effector jaw to push on the base of the otomy feature thereby sliding the otomy feature distally.

6. The electrosurgical end effector of claim 5, wherein the otomy feature is biased by a spring to retract into a retracted position within a nonconductive shroud.

7. An electrosurgical tool for a teleoperated surgical system, the
electrosurgical tool comprising:
a pair of end effector jaws rotatingly coupled together at a pivot axis by a pin, a first end effector jaw of the pair of end effector jaws to pivot about the pivot axis with respect to a second end effector jaw of the pair of end effector jaws;
a slidable otomy feature housed in the second end effector jaw;
an actuation mechanism coupled to the first end effector jaw, the actuation mechanism to pivot the first end effector jaw about the second end effector jaw;
a shaft having a distal end coupled to the pair of end effector jaws, the shaft to extend the pair of end effector jaws into a surgical site; and
an interface base coupled to a proximal end of the shaft, the interface base to couple to a robotic slave, the interface base including a first spool to control at least the first end effector jaw;
wherein the otomy feature is mechanically actuated by pivoting of the first end effector jaw about the second end effector jaw.

8. The electrosurgical tool of claim 7, wherein the otomy feature is mechanically actuated by a drive mechanism in the interface base.

9. The electrosurgical tool of claim 7, wherein pivoting of the first end effector jaw causes a cam portion of the first end effector jaw to push on an end of the otomy feature, sliding the otomy feature distally.

10. The electrosurgical tool of claim 7, further comprising:
a spring coupled to the otomy feature to bias the otomy feature in a retracted position within a nonconductive shroud.

11. The electrosurgical tool of claim 10, further comprising:
a distal stop to hold the spring in place within the nonconductive shroud, the distal stop to prevent the otomy feature from retracting past the distal stop.

12. The electrosurgical tool of claim 10, further comprising:
a collar around the otomy feature to receive a spring force from the spring to bias the otomy feature in a retracted position within the nonconductive shroud.

13. A method of electrosurgery using an electrosurgical end effector in a
teleoperated surgical system, the method comprising:
rotating a first end effector jaw in a first rotational direction about a second end effector jaw at a coupling pin to a first jaw angle with the second end effector jaw, the first jaw angle between the first end effector jaw and the second end effector jaw sufficient to contact a cam portion of the first end effector jaw to an end of a slideable otomy feature slidingly coupled to the second end effector jaw;
rotating the first end effector jaw in the first rotational direction to a second jaw angle greater than the first jaw angle to slide a second end of the otomy feature past a distal end of the second end effector jaw; and
contacting tissue with the otomy feature to perforate the tissue.

14. The method of claim 13, further comprising:
retracting the otomy feature by rotating the first end effector jaw in a second rotational direction opposite the first rotational direction to a third jaw angle lesser than the first jaw angle, allowing a biasing spring to slide the otomy feature to a retracted position inside the second end effector jaw.

15. The method of claim 13, further comprising:
energizing an electrical conductor coupled to the otomy feature.

* * * * *